United States Patent [19]

Aloni et al.

[11] Patent Number: 5,586,058

[45] Date of Patent: Dec. 17, 1996

[54] APPARATUS AND METHOD FOR INSPECTION OF A PATTERNED OBJECT BY COMPARISON THEREOF TO A REFERENCE

[75] Inventors: Meir Aloni, Herzliya; Amir Alon, Yahud; Yair Eran, Rehovot; Itzhak Katz, Givat Shmuel; Yigal Katzir, Holon; Gideon Rosenfeld, Tel Aviv, all of Israel

[73] Assignee: Orbot Instruments Ltd., Yavne, Israel

[21] Appl. No.: 880,100

[22] Filed: Apr. 21, 1992

Related U.S. Application Data

[63] Continuation-in-part of Ser. No. 801,761, Nov. 27, 1991.

[30] Foreign Application Priority Data

Dec. 4, 1990 [IL] Israel .......................................... 96541

[51] Int. Cl.[6] ............................................................ G06K 9/68
[52] U.S. Cl. ........................... 364/552; 382/141; 382/148; 382/151
[58] Field of Search ..................................... 364/150, 151, 364/488–491, 578, 579, 551.01, 551.02, 552, 550; 382/8, 18, 141, 144, 145, 148, 149, 151; 340/825.15; 324/512, 555

[56] References Cited

U.S. PATENT DOCUMENTS

| 4,247,203 | 1/1981 | Levy et al. . | |
|---|---|---|---|
| 4,347,001 | 8/1982 | Levy et al. . | |
| 4,481,664 | 11/1984 | Linger et al. | 382/8 |
| 4,532,650 | 7/1985 | Wihl et al. . | |
| 4,579,455 | 4/1986 | Levy et al. . | |
| 4,628,531 | 12/1986 | Okamoto et al. . | |
| 4,633,504 | 12/1986 | Wihl et al. . | |
| 4,731,855 | 3/1988 | Suda et al. . | |
| 4,764,969 | 8/1988 | Ohtombe et al. | 382/148 |
| 4,794,647 | 12/1988 | Forgues et al. | 382/8 |
| 4,805,123 | 2/1989 | Specht et al. . | |
| 4,926,489 | 5/1990 | Danielson et al. . | |
| 5,163,128 | 11/1992 | Straayer | 382/8 |
| 5,325,443 | 6/1994 | Beatty et al. | 382/149 X |

FOREIGN PATENT DOCUMENTS

| 55-176555 | 12/1980 | Japan . |
|---|---|---|
| 57-22239 | 2/1982 | Japan . |
| 58-206949 | 12/1983 | Japan . |

OTHER PUBLICATIONS

A. Rosenfeld, et al., "Digital Picture Processing", vol. 1, Academic Press, 1982, pp. 36–49.
A. Rosenfeld, et al., "Digital Picture Processing", vol. 1, Academic Press, 1982, pp. 215–217.
Detection and Sub–Piscel Location of Objects in Digitized Aerial Imagery –Mark L. Akey & O. R. Mitchell –Purdue University –(no date).
A Computational Approach To Edge Education John Canny –vol. Pami–8, No. 6, Nov. 1986.
Using Stereo Vision Analysis To Recognize Partially Obscured Objects, Li Jin–Cheng & Yuan Bao–Zung –Beijing China –1988 IEEE.
A Line Extraction Method For Automated Sem Inspection of VLSI Resist –Transactions on Pattern Analysis And Machine Intelligence–shu et al. –vol. 10, No. 1, Jan. 1988.
Locating Industrial Parts With Subpixel Accuracies, Richard A. Young –MI –USA SPIE vol. 728 Optics, Illumination And Image for Machine Vision –1986.
A. Rosenfeld et al, "Digital Picture Processing", vol. 1, Academic Press, 1982, pp. 255 to 304.

*Primary Examiner*—Ellis B. Ramirez
*Assistant Examiner*—Edward Pipala
*Attorney, Agent, or Firm*—Ladas & Parry

[57] ABSTRACT

The present invention seeks to provide an improved system for inspection of and detection of defects in objects such as reticles, photomasks, semiconductor wafers, flat panel displays and other patterned objects. Preferably, the system has two or more stages, whereby the object is examined separately for fine defects, preferably by inspecting a binary level representation of the object, and for ultra fine defects, preferably by inspecting a gray level representation of the object. The system also preferably includes reinspection apparatus for reinspection of detected defects, thereby to reduce the false alarm rate, and for classifying the remaining defects by size, area and type.

27 Claims, 22 Drawing Sheets

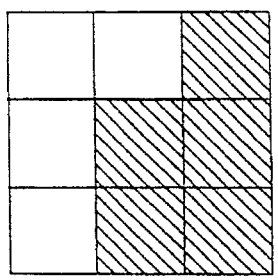
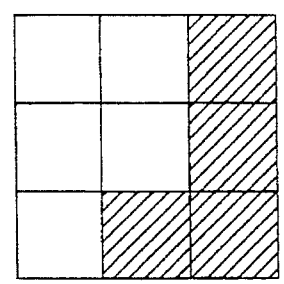
R  FIG. 2A  I
```
1 1 0        1 1 0
1 0 0        1 1 0
1 0 0        1 0 0
```
R  FIG. 2B  I
```
0 0 1        0 0 1
0 1 1        0 0 1
0 1 1        0 1 1
```
−R  FIG. 2C  −I $$\begin{array}{|c|c|c|}\hline 0 & 0 & 0 \\\hline 0 & 0 & 0 \\\hline 0 & 0 & 0 \\\hline\end{array}$$

(R)·(−I)

FIG. 2D $$\begin{array}{|c|c|c|}\hline 0 & 0 & 0 \\\hline 0 & 1 & 0 \\\hline 0 & 0 & 0 \\\hline\end{array}$$

(I)·(−R)

FIG. 2E $$\begin{array}{|c|c|c|}\hline 0 & 0 & 0 \\\hline 0 & 1 & 0 \\\hline 0 & 0 & 0 \\\hline\end{array}$$

| $P_{15}$ | $P_{14}$ | $P_{13}$ | $P_{12}$ | $P_{11}$ |
|---|---|---|---|---|
| $P_{16}$ | $P_4$ | $P_3$ | $P_2$ | $P_{10}$ |
| $P_{17}$ | $P_5$ | $P_0$ | $P_1$ | $P_9$ |
| $P_{18}$ | $P_6$ | $P_7$ | $P_8$ | $P_{24}$ |
| $P_{19}$ | $P_{20}$ | $P_{21}$ | $P_{22}$ | $P_{23}$ |
FIG. 3A
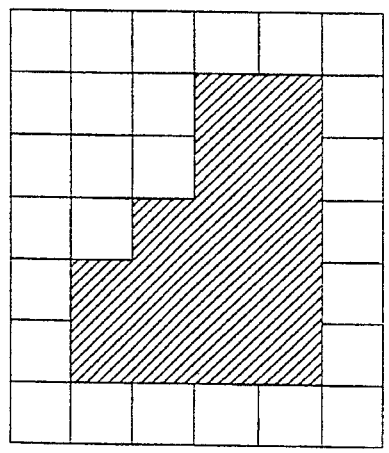
FIG. 3B
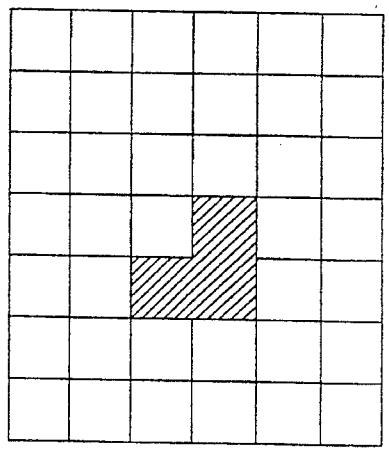
FIG. 3C

▧ E

▧ G

▧ R-I  ▨ I-R

▧ E
▨ H
▨ J

▧ G
▨ K
▨ L

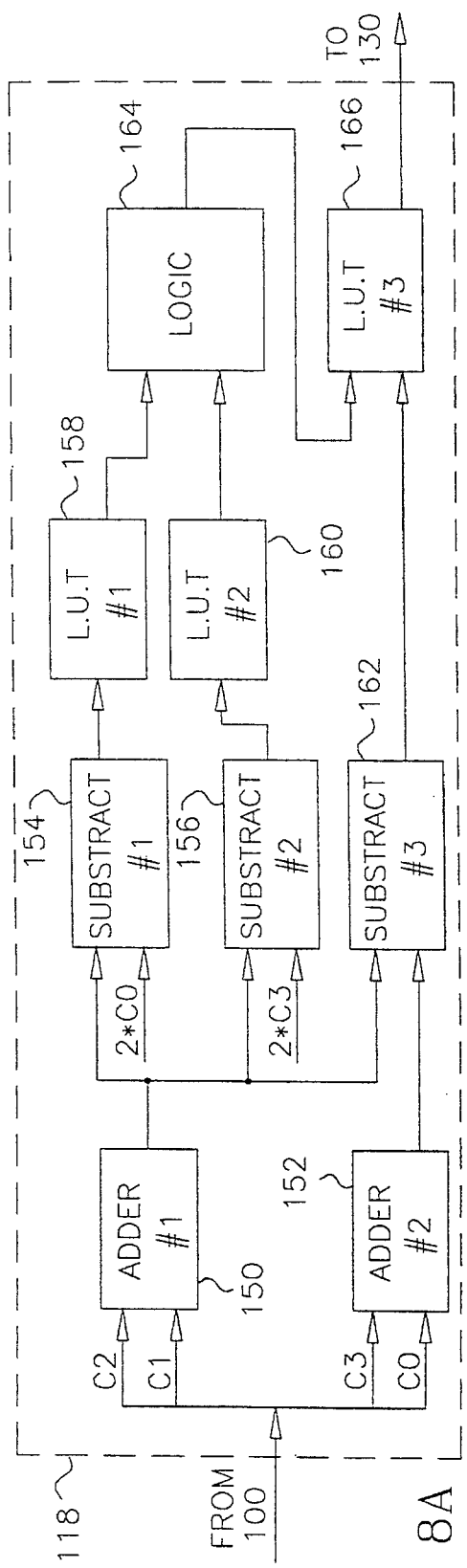
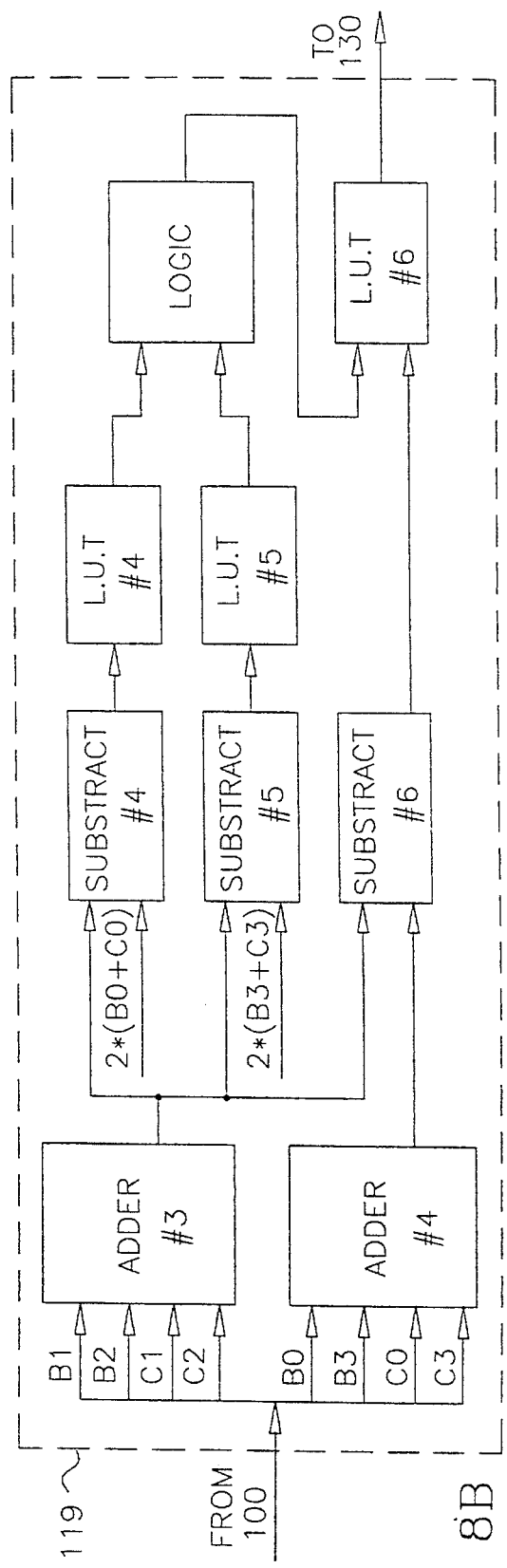
FIG. 8A
FIG. 8B

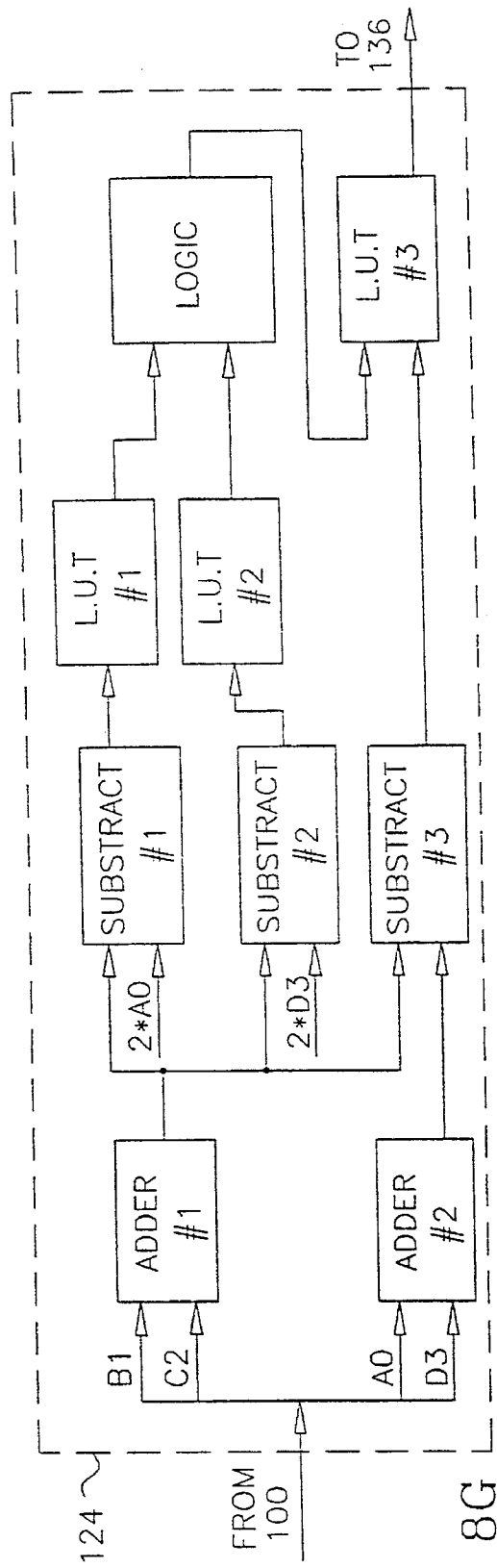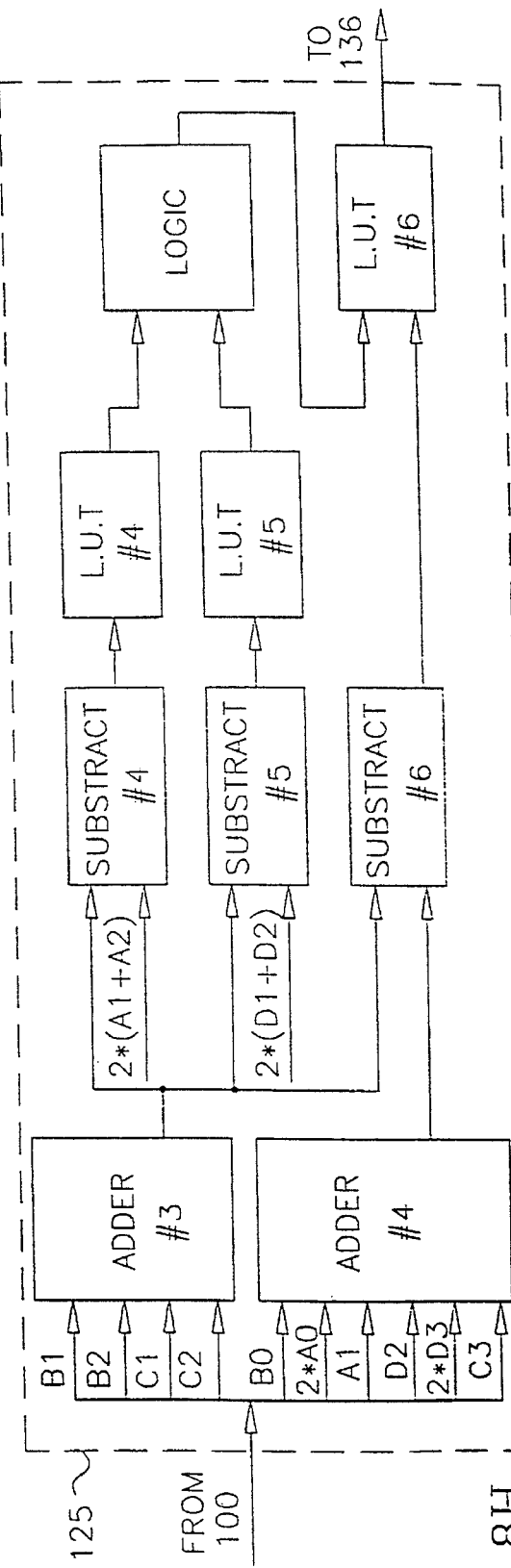
FIG. 8G
FIG. 8H 5,586,058

APPARATUS AND METHOD FOR INSPECTION OF A PATTERNED OBJECT BY COMPARISON THEREOF TO A REFERENCE

This application is a CIP of Ser. No. 07/801,761 filed Nov. 27, 1994.

FIELD OF THE INVENTION

The present invention relates to apparatus and methods for microscopic inspection of articles and more particularly to an apparatus and methods for detecting defects in a VLSI reticle by comparison to a reference.

BACKGROUND OF THE INVENTION

Apparatus and methods for automatically inspecting photomasks of reticles used in manufacturing VLSI circuits have been described in the literature and have been commercially available for a number of years.

These systems generally employ an optical sensor to provide an electronic representation of the inspected object so that a comparison to another similar object or electronic representation can be made. In order to detect non-random, i.e. repeating, defects the comparison is generally made against a known good reference. If the reference is the design database from which the inspected article was manufactured, a generally complete set of defect types may be detected. An inspection system may be characterized by the different types of articles it can inspect, the type of reference it uses, the types and sizes of defects it detects, and the time it requires to inspect a complete article. Modern VLSI technology typically requires the detection of 0.5 micron defects on a single die 5× reticle in 10 minutes.

Inspection apparatus is disclosed in U.S. Pat. Nos. 4,247,203 and 4,347,001, both to Levy et al. The apparatus described in those patents locates faults in the photomask by simultaneously comparing adjacent dies on the photomask and locating differences. Because a known good die is not used in this type of inspection apparatus, only random, i.e. non-repeating, faults are generally identifiable, and not repeating faults.

U.S. Pat. No. 4,579,455, also to Levy et al, describes attempts to improve the detection efficiency of inspection apparatus especially at photomask pattern edges. An area subtraction technique is used to identify defects by detecting differences between substantially duplicate die patterns in a photomask. Two square window matrices of seven rows and seven columns of adjacent pixels are defined for corresponding areas of two die patterns in a single photomask. The center 3×3 matrix of each window matrix is defined as a comparison matrix with each window matrix having twenty five unique subsets of 3×3 adjacent pixels within its boundaries; one in the center and twenty four others that are offset by one or two pixels from the center in one or both directions.

An error value is then calculated for each subset of each matrix by summarizing the squares of the differences between each of the nine pixel values of each subset and the corresponding pixel value of the opposite comparison matrix. If there is no defect, and misalignment between the two representations is less than two pixels, at least one error value will be less than a threshold error value. If none of the twenty five error values relating to one comparison matrix are less than the threshold value, a defect is assumed to be located within the comparison matrix or within the opposite window matrix. The magnitude of the threshold error is then automatically varied according to the number of edges within the window matrices to compensate for edge induced errors.

U.S. Pat. No. 4,532,650 to Wihl et al describes attempts to improve the defect efficiency of inspection apparatus especially near photomask pattern corners. The detection process is based upon using a vector gradient within a matrix to develop candidate and canceller information for each representation. This information is then logically manipulated to qualify the data obtained and to determine whether or not a defect has been detected.

U.S. Pat. No. 4,805,123 to Specht et al describes a photomask and reticle inspection system in which a first stream of data representing the image content of a selected surface area of an object to be inspected is compared to a second stream of data representing the intended image content of the selected surface area of the object. After misalignment between stored portions of the two streams of data is detected and corrected, using shifts of an integral number of pixels and/or subpixel interpolation methods, subportions are compared in order to detect differences therebetween in excess of a predetermined threshold.

U.S. Pat. No. 4,926,489 to Danielson et al. describes a die-to-database reticle inspection system including timing control means which is responsive to misalignment between the inspected object and the database. The timing control means is used to generate control signals which adjust the relative output signal rates of the scanner and the database thereby maintaining the misalignment below a predetermined limit.

SUMMARY OF THE INVENTION

The present invention seeks to provide an improved system for inspection of and detection of defects in objects such as reticles, photomasks, semiconductor wafers, flat panel displays and other patterned objects. Preferably, the system has two or more stages, whereby the object is examined separately for fine defects, preferably by inspecting a binary level representation of the object, and for ultra fine defects, preferably by inspecting a gray level representation of the object.

The two-stage inspection system has the advantage of allowing different algorithms to be used for fine defect detection and for ultra fine defect detection, each algorithm being generally optimal for defects of the size it is intended for but not necessarily for defects of other sizes. The system may make die to database comparisons or die to die comparisons.

The system also preferably includes reinspection apparatus for reinspection of detected defects, thereby to reduce the false alarm rate, and for classifying the remaining defects by size, area and type. Preferably the system also includes diagnostic apparatus for performing diagnostic functions such as inspecting the flow of information through the system and diagnosing which component of the system may be misoperating.

There is thus provided in accordance with a preferred embodiment of the present invention an inspection method including the steps of providing a patterned object to be inspected and compared with a reference, inspecting the patterned object and providing an output of information relating to the visual characteristics of the patterned object, comparing binary level information relating to the visual characteristics of the patterned object to binary level information relating to the visual characteristics of the reference, and comparing gray level information relating to the visual characteristics of the patterned object to gray level information relating to the visual characteristics of the reference.

There is also provided in accordance with a further preferred embodiment of the present invention an inspection method including the steps of providing a patterned object to be inspected and compared with a reference, inspecting the patterned object and providing an output of information relating to the visual characteristics of the patterned object, and providing an output indication of differences between the patterned object and the reference, the step of providing including the steps of sensing hill profiles and valley profiles in information relating to the visual characteristics of the patterned object, sensing hill profiles and valley profiles in information relating to the visual characteristics of the reference and providing a defect indication when a hill profile or a valley profile of at least a sufficient level is sensed for a given location in the patterned object and not for a corresponding location in the reference.

There is also provided in accordance with a preferred embodiment of the present invention an inspection method for providing an output indication of differences between an patterned object and a reference and including the steps of providing a patterned object to be inspected and compared with a reference, comparing binary level information relating to the visual characteristics of the patterned object to binary level information relating to the visual characteristics of the reference and filtering out differences within a selected magnitude range.

There is further provided in accordance with yet a further preferred embodiment of the present invention an inspection method including the steps of providing a patterned object to be inspected and compared with a reference, initially inspecting the patterned object and providing an output of information relating to visual characteristics of the patterned object, providing an output indication of differences between the patterned object and the reference representing possible defects, and simultaneously storing information regarding visual characteristics of areas of the patterned object at which possible defects are indicated.

Further in accordance with a preferred embodiment of the present invention, the method also includes the step of automatically carrying out a further inspection of the areas of the patterned object using the stored information.

Still further in accordance with a preferred embodiment of the present invention, the step of automatically carrying out includes the step of comparing at least some of the areas to a reference.

Additionally in accordance with a preferred embodiment of the present invention, the method also includes the step of displaying the stored information to an operator.

In accordance with still a further preferred embodiment of the present invention there is provided an inspection method including the steps of providing a patterned object to be inspected and compared with a reference, inspecting the patterned object and providing a representation of visual characteristics of the patterned object, providing an output indication of differences between the patterned object and a representation of visual characteristics of the reference, at least one of the inspecting step and the difference indicating step including the step of providing at least one subsystem which modifies at least one of the representations, thereby to provide a plurality of representations of at least one of the patterned object and the reference, and inspecting the flow of information through the inspecting apparatus and the difference indicating apparatus and including comparing individual ones from among the plurality of representations.

There is also provided in accordance with a further preferred embodiment of the present invention an inspection method including the steps of providing a patterned object to be inspected and compared with a reference, inspecting the patterned object and providing an output of information relating to the visual characteristics of the patterned object, providing an indication of differences between the patterned object and the reference, and automatically carrying out a second inspection of at least some areas of the patterned object thereby to complement the providing step by enhancing the output indication of differences provided by the providing step.

There is further provided in accordance with still a further preferred embodiment of the present invention an inspection system including apparatus for comparing an inspected object to a reference and providing an output of information relating to the visual characteristics of the inspected object, binary level comparison apparatus for comparing binary level information relating to the visual characteristics of the inspected object to binary level information relating to the visual characteristics of the reference, and gray level comparison apparatus for comparing gray level information relating to the visual characteristics of the inspected object to gray level information relating to the visual characteristics of the reference.

Further in accordance with a preferred embodiment of the present invention, the system also includes apparatus for providing information relating to the visual characteristics of the reference.

Still further in accordance with a preferred embodiment of the present invention, the gray level comparison apparatus includes apparatus for converting binary level information relating to visual characteristics of the reference into gray level information.

Additionally in accordance with a preferred embodiment of the present invention, the binary level comparison apparatus is operative to sense differences of at least a first minimum size and the gray level comparison apparatus is operative to sense differences of at least a second minimum size smaller than the first minimum size.

Still further in accordance with a preferred embodiment of the present invention, the gray level comparison apparatus includes first apparatus for sensing hill profiles and valley profiles in the information relating to the visual characteristics of the inspected object, second apparatus for sensing hill profiles and valley profiles in the information relating to the visual characteristics of the reference, and apparatus for providing a defect indication when a hill profile or a valley profile of at least a sufficient level is sensed for a given location in the inspected object and not for a corresponding location in the reference.

Further in accordance with a preferred embodiment of the present invention, the system also includes apparatus responsive to selected information indicating the presence of selected features at locations in the reference for preventing provision of an output indication of difference in respect of those locations.

Still further in accordance with a preferred embodiment of the present invention, the location in an individual one of the reference and the inspected object is larger in area than the corresponding location in the other one of the reference and the inspected object.

Additionally in accordance with a preferred embodiment of the present invention, the second apparatus for sensing is operative with a higher sensitivity than the sensitivity of the first apparatus, thereby to reduce the false alarm rate of the apparatus for providing a defect indication.

There is also provided in accordance with yet a further preferred embodiment of the present invention an inspection system for providing an output indication of differences between an inspected object and a reference and including binary level comparison apparatus for comparing binary level information relating to the visual characteristics of the inspected object to binary level information relating to the visual characteristics of the reference, and apparatus for providing an output indication of differences and including apparatus for filtering out differences within a selected magnitude range.

Further in accordance with a preferred embodiment of the present invention, the binary comparison apparatus includes at least one of the following: at least one SUBTRACTION logical operator, and at least one XOR logical operator.

Still further in accordance with a preferred embodiment of the present invention, the apparatus for filtering includes an EROSION operator and/or an ACCEPTANCE operator.

Additionally in accordance with a preferred embodiment of the present invention, the apparatus for filtering includes apparatus for differentiating between differences between the inspected object and the reference on the basis of the location of each difference relative to at least one edge of an adjacent binary shape defined in at least one of the inspected object and the reference.

There is also provided in accordance with yet a further preferred embodiment of the present invention an inspection system including apparatus for initially inspecting an inspected object and providing an output of information relating to visual characteristics of the inspected object and apparatus for providing an output indication of differences between the inspected object and a reference, representing possible defects, and for simultaneously storing information regarding visual characteristics of areas of the inspected object at which possible defects are indicated.

Further in accordance with a preferred embodiment of the present invention, the system also includes further inspection apparatus for automatically carrying out a further inspection of the areas of the inspected object using the stored information.

Still further in accordance with a preferred embodiment of the present invention, the apparatus for automatically carrying out includes apparatus for comparing at least some of the areas to a reference.

Additionally in accordance with a preferred embodiment of the present invention, the system also includes apparatus for displaying the stored information to an operator.

Still further in accordance with a preferred embodiment of the present invention, the system also includes apparatus for providing information relating to the visual characteristics of the reference.

Further in accordance with a preferred embodiment of the present invention, the apparatus for storing is operative to store the information provided by the apparatus for initially inspecting.

Still further in accordance with a preferred embodiment of the present invention, the apparatus for storing is operative to store an output indication of differences received from the apparatus for providing an output indication of differences.

Additionally in accordance with a preferred embodiment of the present invention, the further inspection apparatus includes apparatus for classifying at least some of the possible defects in accordance with at least one criterion.

Still further in accordance with a preferred embodiment of the present invention, the apparatus for carrying out a second inspection is characterized in that the second inspection of areas of an inspected object may be initiated while the apparatus for providing an output indication is operating.

Further in accordance with a preferred embodiment of the present invention, the apparatus for carrying out a second inspection is characterized in that the second inspection of areas of an inspected object may be initiated while the apparatus for providing an output indication is operating on the inspected object.

There is also provided in accordance with a further preferred embodiment of the present invention an inspection system including inspecting apparatus for inspecting an inspected object and providing a representation of visual characteristics of the inspected object, difference indicating apparatus for providing an output indication of differences between the inspected object and a representation of visual characteristics of a reference, at least one of the inspecting apparatus and the difference indicating apparatus defining at least one subsystem which modifies at least one of the representations, thereby to provide a plurality of representations of at least one of the inspected object and the reference, and information flow inspection apparatus for inspecting the flow of information through the inspecting apparatus and the difference indicating apparatus and including apparatus for comparing individual ones from among a plurality of representations of an object.

Further in accordance with a preferred embodiment of the present invention, the information flow inspection apparatus includes apparatus for providing input directly to a selected one of the at least one subsystems.

Still further in accordance with a preferred embodiment of the present invention, the input includes a representation of visual characteristics of one of the inspected object and reference outputs by a subsystem upstream of the selected subsystem.

Further in accordance with a preferred embodiment of the present invention, the input includes a test pattern.

Still further in accordance with a preferred embodiment of the present invention, the information flow inspection apparatus includes apparatus for inspecting the output of a selected one of the at least one subsystems.

Additionally in accordance with a preferred embodiment of the present invention, the system includes apparatus for providing a representation of information relating to visual characteristics of a selected object to a selected one of the at least one subsystems, thereby to provide a plurality of representations of information related to visual characteristics of the selected object.

There is also provided in accordance with still a further preferred embodiment of the present invention an inspection system including apparatus for comparing an inspected object to a reference and providing an output of information relating to the visual characteristics of the inspected object, first apparatus for providing an indication of differences between the inspected object and the reference, and second apparatus for automatically carrying out a second inspection of at least some areas of the inspected object and for complementing the first apparatus and including apparatus for enhancing the output indication of differences provided by the first apparatus.

Further in accordance with a preferred embodiment of the present invention, the apparatus for enhancing includes apparatus for preventing provision of the output indication of difference in at least some areas of the inspected object, thereby to reduce the false alarm rate of the first apparatus.

Still further in accordance with a preferred embodiment of the present invention, the second apparatus includes apparatus for providing an output indication of differences between the inspected object and the reference not detected by the first apparatus.

There is further provided in accordance with still another preferred embodiment of the present invention alignment apparatus including apparatus for providing binary level information relating to a patterned object to be inspected, thereby to define an inspected object channel, apparatus for providing binary level information relating to a reference, thereby to define a reference channel, and apparatus for aligning the inspected object channel and the reference channel using the binary level information.

Further in accordance with a preferred embodiment of the present invention, the apparatus for aligning includes first apparatus for comparing a portion of the binary level information relating to the inspected object to a corresponding portion of the binary level information relating to the reference, thereby to provide an output indication of misalignment, and second apparatus for receiving the output indication of misalignment from the first apparatus and for aligning the corresponding portions of the binary level information relating to the inspected object and the reference.

Further in accordance with a preferred embodiment of the present invention, the system also includes apparatus for receiving information relating to the visual characteristics of the reference from a database precursor of the reference.

Still further in accordance with a preferred embodiment of the present invention, the apparatus for inspecting includes apparatus for inspecting the reference and providing information relating to the visual characteristics of the reference.

Additionally in accordance with a preferred embodiment of the present invention, the system also includes apparatus for inspecting the reference and providing information relating to the visual characteristics of the reference.

Still further in accordance with a preferred embodiment of the present invention, the apparatus for inspecting includes apparatus for varying the magnification at which at least the inspected object is inspected.

Further in accordance with a preferred embodiment of the present invention, the apparatus for inspecting also includes apparatus for automatically controlling, as a function of the magnification, parameters relating to the inspection of at least the inspected object.

Further in accordance with a preferred embodiment of the present invention, the patterned object includes an individual one of the following group: a flat panel display, a reticle, a printed circuit board, a semiconductor wafer, a photomask, and a blank of any of the above.

In accordance with still a further preferred embodiment of the present invention, there is provided an inspection system including apparatus for providing at least one representation of the visual characteristics of an inspected object, first apparatus for comparing an individual one of the at least one representations of the inspected object to a reference and for providing an output indication of differences, and second apparatus for comparing an individual one of the at least one representations to a reference, thereby to complement the first apparatus by enhancing the indication of differences provided by the first apparatus.

According to still a further preferred embodiment of the present invention, there is provided diagnostics apparatus for diagnosing the operation of an information processing system, the information processing system including a plurality of subsystems, each individual one from among the plurality of subsystems being operative to receive a first representation of information to be processed and to output a second representation of the information to be processed, the apparatus including information flow diagnosing apparatus for comparing individual ones from among the plurality of representations.

Still further in accordance with a preferred embodiment of the present invention, the information flow diagnosing apparatus is synchronized with the information processing system.

Additionally in accordance with a preferred embodiment of the present invention, the information flow diagnosing apparatus is electronically integrated with the information processing system.

Further in accordance with a preferred embodiment of the present invention, the information flow diagnosing apparatus includes apparatus for comparing individual ones from among the plurality of representations in real time.

Further in accordance with a preferred embodiment of the present invention, the apparatus also includes apparatus for providing input, such as a test pattern, directly to a selected one of the at least one subsystems.

Still further in accordance with a preferred embodiment of the present invention, the apparatus also includes apparatus for receiving the output of a selected one of the at least one subsystems.

Additionally in accordance with a preferred embodiment of the present invention, the apparatus for receiving includes apparatus for recording the output of the selected one of the least one subsystems and apparatus for off-line processing of the recorded output.

BRIEF DESCRIPTION OF THE DRAWINGS

The present invention will be understood and appreciated from the following detailed description, taken in conjunction with the drawings in which:

FIGS. 2A–2F are conceptual illustrations of stages of a preferred algorithm for the binary defect detector 32 of FIG. 1;

FIG. 3A illustrates a 5×5 pixel neighborhood;

FIGS. 3B–3C are conceptual illustrations of a binary shape before and after erosion in the binary defect detector 32 of FIG. 1;

FIGS. 8A–8H are block diagrams of the defect detection units 118–125 of FIG. 7;

DETAILED DESCRIPTION OF PREFERRED EMBODIMENTS

Figure 1A:
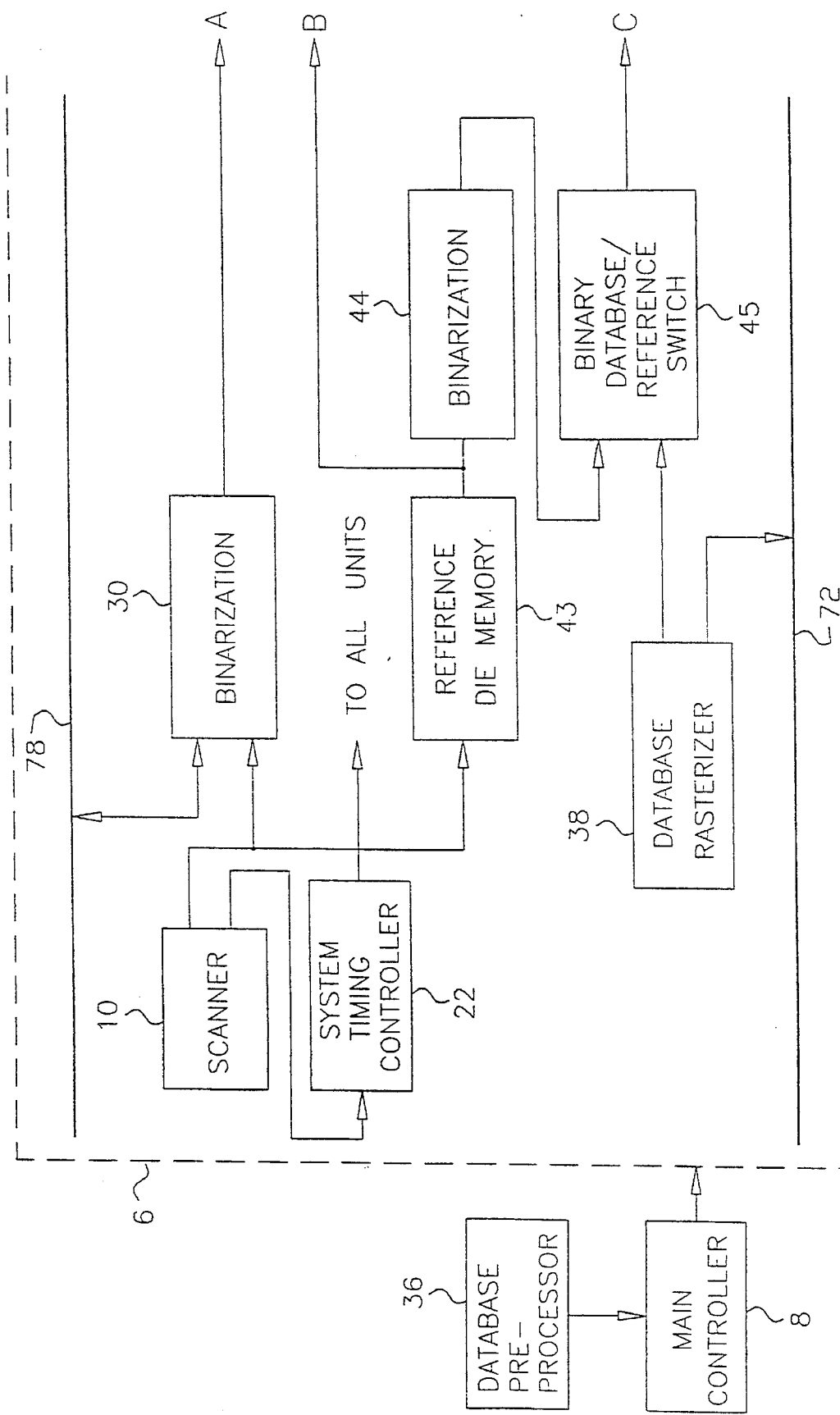
FIGS. 1/1 and 1/2 are, composed of FIGS. 1A and 1B, generalized block diagrams of apparatus constructed and operative in accordance with a preferred embodiment of the present invention.
Figure 1B:
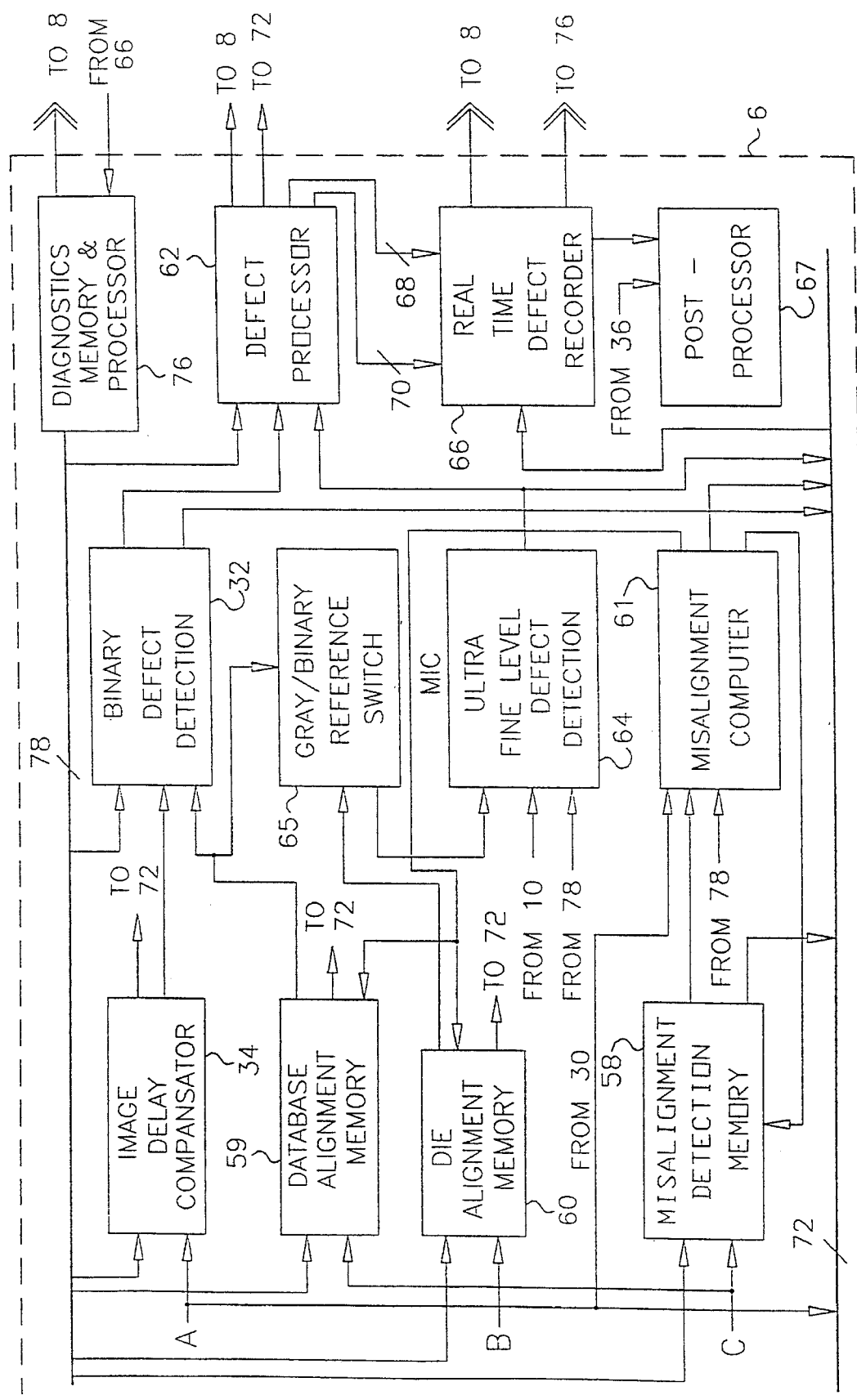

Reference is now made to FIG. 1, composed of FIGS. 1A and 1B, which is a conceptual block diagram of an inspection system 6 constructed and operative in accordance with a preferred embodiment of the present invention. The inspection system 6 is controlled by a main controller 8 and generally comprises means for scanning an inspected object, defining an inspected channel, and means for providing a reference such as a reference die or a database, defining a reference channel. Inspection system 6 also generally comprises means for aligning the inspected and reference channels, means for comparing the inspected and reference channels in order to provide an output indication of defects in the inspected object, and, preferably, means for diagnosing the function of the system.

The real time means for comparing the two channels is preferably operative on two levels, termed hereinbelow "fine" defect detection and "ultra-fine" defect detection, and is also preferably operative to record information regarding defects detected in real time, thereby to enable subsequent re-examination of these defects in order to reduce the false alarm rate of the defect detection process. Re-examination of the defects is preferably not executed in real time. Once detected, defects may be categorized and/or repaired. More specifically, the inspection system 6 preferably includes the following components:

A scanner 10 is operative to electro-optically scan an object to be inspected and to output a gray-level digital representation thereof, preferably of 8 bit depth. A representation of a scanned portion of the object is preferably arranged as a two dimensional array having n lines and m pixels per line. A typical number of pixels per line is 1024. The scanner 10 preferably scans successive, equally distanced lines. The time required to scan a single line is termed herein a "line time". The "line time" may not be a constant but rather may vary linearly as a function of the instantaneous scanner velocity. The scanner 10 is described in detail hereinbelow with reference to FIGS. 14 and 15.

The scanner 10 provides an output indication of timing to all relevant components of the system, as shown, via a timing controller 22 which is operative to synchronize the various components of the system in accordance with the timing of the scanner 10. The scanner timing output indication typically comprises the following three signals:

a. A "start of scan" signal indicative of the time at which scan of the inspected object is initiated;

b. A "grab line" signal indicative of the time at which scan of the current line is initiated; and c. A "grab pixel" signal indicative of the time at which scan of the current pixel is initiated.

The 8-bit scanner output is binarized by a binarization unit 30 such as the binarization system shown and described in Applicants' copending U.S. patent application Ser. No. 684,583, the disclosure of which is incorporated herein by reference. As explained in that document, the output of the binarization unit 30 is a binary digital representation of the object to be inspected at a higher resolution than the gray digital representation received by the binarization unit 30. The pixels of the 8 bit gray representation of the object to be inspected which are received by binarization unit 30 are termed herein big pixels (BP) or large pixels (LP). The pixels of the binary representation of the object to be inspected which are provided by binarization unit 30 are termed herein small pixels (SP).

The output of binarization unit 30 is received by a binary defect detector 32 via an image delay compensator 34. The compensator 34 is operative to delay the output of binarization unit 30 by a fixed time interval of typically $5 \times 10^{-4}$ sec. so that each portion of output, representing the inspected object, is received by the binary defect detector 32 at the same time as the corresponding portion of the information relating to the reference. The information relating to the reference is received by binary defect detector 32 from an database alignment memory 59 as explained in more detail below.

The binary defect detector 32 is a fine level defect detector and is operative to detect, in the inspected object, defects of a selected minimum size, typically 0.7–1.4 pixels. Binary defect detector 32 may also be operative to detect certain types of defects, such as pin holes and pin dot type defects, which are somewhat smaller than the selected minimum size.

A database preprocessing station 36 stores or otherwise provides information regarding a database to which the object undergoing inspection may be compared, if a die to database process is employed. Alternatively, the inspected object may be compared using a die to die process, as explained in more detail hereinbelow. Preprocessing station 36 typically converts the database, which may be in a vectorial or polygonal format such as MEBES or GDSII and may have a relatively high resolution, to an internal format. The converted database information is then provided, via a local area network (LAN), to the main controller 8. Controller 8 passes on the newly formatted information via vector commands to a database rasterizer 38 which provides a binary level Paster representation of the database. The pixels of the binary level database provided by rasterizer 38 are termed herein small pixels (SP).

Alternatively, a reference other than a database may be employed. For example, if the object to be inspected comprises a plurality of identical areas, a die to die type procedure may be employed in which a first such identical area may be compared to each of the other identical areas and may serve as a reference therefor. Preferably, a portion of gray level information regarding the reference die is read by the scanner 10 and stored in a reference die memory 43. The stored information is binarized by a binarization unit 44 which may be similar to binarization unit 30. The corresponding portion of information regarding the inspected die is then read by the scanner, binarized by binarization unit 30 and compared with the output of binarization unit 44. Preferably, all scanned reference die information is retained in reference die memory 43 and is not discarded, in order to allow postprocessing of detected defects without rescanning the reference die, as explained in more detail hereinbelow with reference to FIG. 13.

Preferably a switch 45 is provided for selecting whether the reference information provided to misalignment detection memory 58 (see below) originates from a database, as in die to database comparison methods, or from a die, as in die to die comparison methods.

The binary database information or binarized reference information selected by switch 45 is provided to an automatic registration subsystem comprising a misalignment detection memory 58, a database alignment memory 59, a die alignment memory 60 and a misalignment computer 61. The automatic registration subsystem is operative to align or provide registration between the reference channel and the inspected object channel. The automatic registration subsystem is operative to correct for continuous misregistration phenomena, such as irregular velocity of the scanner, system vibrations and thermal drift and also for misregistration due to discontinuities in the inspected channel such as stepping errors or sparse geometries.

In the forgoing discussion of the automatic registration subsystem, the term "line" is intended to refer to an individual sequence of pixels, typically comprising 1024 pixels, output by the CCD array of the scanner 10 during a single "line time".

The binary database information and the binarized scanner output representing the inspected object enter the automatic registration computer 61. This unit together with the misalignment detection memory 58 operate in a servo type manner to compute the misregistration between the reference channel and the inspected channel. Registration correction commands are subsequently applied to the contents of database alignment memory 59 and of die alignment memory 60, thereby to provide aligned representations of the database and the die respectively. The registration correction commands are operative to determine the addresses according to which information should be read from the alignment memories 59 and 60.

The provision of two separate memory arrays, the first memory array comprising misalignment detection memory 58 and the second memory array comprising alignment memories 59 and 60, has the advantage of giving the automatic registration subsystem a look-ahead capability. Specifically, each individual portion of the reference data stream arrives at the registration computer 61 and substantially simultaneously is stored at alignment memories 59 and 60. The "delay" introduced by alignment memories 59 and 60 allows registration computer 61 to issue suitable registration commands to the alignment memories 59 and 60, thereby to align the individual portion of the reference data stream before it reaches defect detectors 32 and 64 (see below). This look ahead capability allows the system to recover more rapidly from misalignments which develop during discontinuities in the inspected data stream such as stepping errors or sparse geometries, by looking ahead to a patterned non-blank area.

The purpose of automatic registration is to achieve a global match between a binary representation of the image and the database, on-the-fly, based on some neighborhood around the currently scanned data. A registration vector is computed for each line of scanned image pixels representing the displacement to be applied to the database pixels so as to correctly align them with respect to the corresponding scanned image pixels.

A preferred binary alignment method, in which local measurements of displacement are used to compute a global measurement of displacement, comprises the following two steps:

1. Local displacement measurement: Quantification of the local displacement along a plurality of axes, preferably two orthogonally disposed axes, in a small "local" window around the current line of the scanned image. Any suitable method may be employed to identify and quantify the local displacement, such as use of XOR operators and subsequent counting of the length of the XOR operator along each of the axes. A preferred size for the window is approximately 5–10 lines. The measurement is preferably carried out in conjunction with a feature detector which is operative to detect features, such as edges which are non-parallel to the axes and corners, which may require special treatment.

2. Global displacement computation: Quantification of the global displacement along two orthogonally disposed axes, in a large "global" window around the current line, typically comprising approximately 12 lines, using the local measurements derived from each of the plurality of "local" windows contained within the "global" window.

A preferred method for carrying out the first, local step is as follows:

The binary representation of the image is typically provided at the same resolution as the database resolution, which may be effected within binarization unit 30, as explained in detail in Applicant's copending U.S. application Ser. No. 684,583. The local displacement of the image I with respect to the database D may be computed by performing subtractions I–D and D–I, as illustrated in the example below, and subsequently determining the lengths of the runs in the streams I–D and D–I. It should be noted that the length may be positive or negative depending on the relative position of the image with respect to the database. Preferably, not every row of binary pixels, but rather only one row from among each few adjacent binary pixel rows of the streams I–D and D–I, is sampled, along each of the plurality of axes.

A sample computation of local displacement in a window which, for purposes of illustration, is seen to contain only 3×13 pixels, is as follows:

| I | D |
|---|---|
| 0 1 1 1 0 0 0 1 1 1 1 0 0 | 1 0 0 1 1 1 1 0 0 0 0 0 1 |
| 1 1 1 1 0 0 0 0 1 1 1 1 1 | 1 0 0 1 1 1 1 1 0 0 0 0 1 |
| 1 1 1 0 0 0 0 1 1 1 1 1 1 | 1 0 0 1 1 1 1 1 0 0 0 0 1 |

The two matrices respectively represent portions of three corresponding binary pixel rows of the inspected object I and of the reference or database D. The sampled or current row is the middle row.

(I–D) in the x direction is: 0 1 1 0 0 0 0 0 1 1 1 1 0

There are two runs, of length 2 and 4 respectively.

(D–I) in the x direction is: 0 0 0 0 1 1 1 1 0 0 0 0 0

There is one run, of length 4.

Analogous computations may be carried out along other axes, such as the y axis.

Preferably, a filtering operation is performed on the length values of the detected runs, and thereby some of the length values are filtered out. The remaining length values are termed herein "valid".

The filtering process is preferably based on the following principles:

First, a threshold value is defined which determines the largest expected run length value. Run length values exceeding this threshold are filtered out.

Second, a feature detector is provided that detects "problem zones" containing problematic features such as edges which are non-parallel to the axes and corners. Run length values overlapping such problem zones, even partially, are filtered out.

Preferably, the feature detector is operative to inspect pixels along the edges of binary shapes in the reference data and to mark the problematic features. This may be carried out by considering the two slopes respectively joining each edge pixel to two adjacent pixels along the edge. If the two slopes are nonequal, then a corner is identified. Also, the value of the slopes separately and in combination indicates the orientation of the edge relative to the axes. The two adjacent pixels used for slope computations may be the two pixels directly adjacent to the current edge pixel or may alternatively be separated from the current edge pixel by one or two pixels.

These operations may be implemented by creating a LUT which stores most or all possible configurations of a k×k vicinity of a current pixel, where typical values for k are approximately 3 to 5. The LUT labels each such configuration as "corner", "diagonal", i.e. non-parallel to the axes, or "parallel", i.e. parallel to the axes. Preferably, the "parallel" label is provided with an indication of the axis to which the configuration is parallel. "Corner" and "diagonal" labels are both referred to herein as "invalid" labels. A "parallel" label is referred to herein as an "invalid" label.

Preferably, when a particular configuration is marked as invalid, the invalid mark is applied not only to the current pixel but is also propagated to a neighborhood, which may be approximately 12 lines in size, of the current pixel. This is done in order to compensate for misalignment between the reference and scanned (inspected) channels.

A preferred method for computing slopes and corner angles is described in *Digital Picture Processing* by A. Rosenfeld and A. Kak, Academic Press, 1982, Vol. 1, pp. 257 onward, the disclosure of which is incorporated herein by reference.

A third principle of the filtering process is that a threshold value is defined which determines the largest expected mean run length value in a local window. If the mean run length value in a particular local window exceeds this threshold value, all run length values in that local window are filtered out. This threshold value may not be constant. Preferably, the threshold value is an increasing function of the number of lines preceding the present line yielding no valid run lengths, such as blank lines.

The output of the local displacement measurement step for each local window is preferably:

(a) the number of valid runs; and (b) the algebraic sum of the lengths of the runs.

A preferred method for carrying out the second, global step of the binary alignment method is by computing a global registration vector as follows:

a. For each global window, the mean run length, for all valid runs in that global window, is computed.

b. The sequence of mean run lengths for a sequence of global windows is preferably smoothed using a conventional smoothing function.

The width of a global window is preferably at least half of the scan width and its length may be a few dozen lines.

The smoothing function may comprise any suitable function such as either of the following:

1. A threshold function for limiting the frequency and amplitude of displacement vector fluctuations as a function of the number of valid run length measurements. This threshold value may not be constant. Preferably, the threshold value is an increasing function of the number of lines preceding the present line which yielded no valid run lengths, such as blank lines.

2. An adaptive filter such as an LMS filter may be used to monitor periodic fluctuations in the displacement vector. This method may be used to partially overcome the problem of blank lines in which little or no valid information is available.

In the preceding discussion, the terms "registration" and "displacement" have been used generally interchangeably.

A detailed description of aspects of the local displacement measurement step and the global displacement computation step is provided in Appendix 1 (not printed).

Appendix 2 (not printed) to the present specification is a software implementation of a preferred embodiment of an automatic registration subsystem.

Referring again to FIG. 1, fine defect detector 32 receives the aligned binary representation of the reference from database alignment memory 59, compares it to the binary output of binarization unit 30, which represents the object to be inspected, and provides an output indication of fine defects to a defect processing unit 62.

An ultra fine level defect detector 64, referred to hereinbelow as the "MIC" or microscopic unit, is operative to detect defects of a size below the minimum size defect detectable by fine level defect detector 32. Ultra fine defect detector 64 preferably somewhat overlaps fine defect detector 32 in range, in that it also is capable of detecting defects of a size somewhat above the minimum defect size defined by fine level detector 32. Preferably, the defect detector 64 is operative to detect defects of size approximately 0.5–1.5 pixels.

Preferably, the fine level defect detector 32 is operative to receive and compare binary representations of the reference and inspected object, whereas the ultra fine level defect detector 64 is operative to receive and compare gray-level representations of the reference and inspected objects. Ultra fine level defect detector 64 receives the aligned representation of the reference via a switch 65 which is operative to select whether the reference information originates from a database, as in die to-database comparison methods, or from a die, as in die to die comparison methods. In the first instance, the aligned representation of the reference database is received by detector 64 from database alignment memory 59. In the second instance, the aligned representation of the reference die is received by detector 64 from die alignment memory 60.

Ultra fine level defect detector 64 upgrades the aligned representation, if binary, as in the case of a die to database process, to a gray-level representation. Fine level defect detector 64 compares the gray-level representation of the reference to the gray-level representation of the inspected object provided by the scanner 10, and provides an output indication of ultra fine level defects to defect processing unit 62.

Preferably, the defect processing unit 62 is operative to compare information from the detectors 32 and 64, such that if a defect, such as a defect the size of a single pixel, is identified by both detectors, the "double indication" of this defect is appropriately combined into a single indication.

In the shown embodiment, defect processing unit 62 receives defect indications from two detectors, fine detector 32 and ultra fine detector 64. However, it is appreciated that the defect processing unit may receive defect indications from any suitable number and type of detectors, if multiple level detection, rather than two level detection, is desired.

Preferably, defect processing unit 62 interfaces with a real time recording unit 66 which is operative to record in real time an image of each putative defect identified by defect detectors 32 and 64. Subsequently, software implemented defect analyzing algorithms are employed in a postprocessing unit 67 in order to reduce the false alarm rate of the defect detection process. Since only a relatively small number of locations within the representation of the inspected object (those identified as putative defects) need be analyzed, the analysis carried out by postprocessing unit 67 need not be in real time, thereby enabling more sophisticated post-processing analysis. Postprocessing unit 67 is described in more detail hereinbelow with reference to FIG. 13.

The defect processor 62 is operative to transform each received defect indication from defect detection units 32 and 64 into a trigger signal and a defect coordinate signal which are provided to defect recorder 66 over channels 68 and 70 respectively. The trigger signal is indicative of the component (either fine level unit 32 or ultra fine level unit 64) which identified the defect. The defect coordinate signal provides an indication of the location of the defect, preferably comprising an indication of the line/s and pixel/s within the line/s at which the defect occurs.

According to a preferred embodiment of the present invention, real time recorder 66 interfaces with the output busses of substantially all of the system components via an image bus 72, thereby to allow real time recording of the flow of information throughout the entire system. The real time recordings of the output images and indications provided by the various system components are provided to a diagnostics memory and processor 76 which is operative to monitor and diagnose flaws in the operations of the various components of inspection system 6. According to a preferred embodiment of the present invention, the diagnostics memory and processor 76 interfaces with a test bus 78 which inputs to all components of inspection system 6, thereby to allow test images or random patterns to be injected into any component of the inspection system 6.

Preferably, means are provided for displaying representations recorded by recording unit 66, such as representations of individual defects, to an operator, thereby allowing the operator to perform a variety of operator controlled operations such as defect detection system diagnostics, defect verification and elimination, and defect classification. Preferably, representations of a particular portion of a particular object may be displayed while the system is inspecting a different portion of that object or even while the system is inspecting a different object.

Appendix 3 (not printed) to the present specification is a software implementation of a preferred embodiment of the real time recording unit 66 of FIG. 1.

Diagnostic memory/processor 76 is operative to store synthetic and real images corresponding to representations of the inspected object. These representations may be generated from outside the system or by the real time recorder 66. Diagnostics memory/processor 76 may also act as a test pattern generator, injecting test patterns into a selected subsystem through test bus 78.

Under control of the main controller 8 each component of the inspection system 6 processes the input arriving from the test bus 78 substantially as though it were a real input from the image bus 72. The output from any such process may be recorded by the real time recorder 66 and analyzed by post processor 67. If desired, the output of the process may be displayed to the operator. The data transferred along the test bus 78 from diagnostics memory/processor 76 may comprise a test pattern which has been specially generated for diagnostic purposes. By examining the output of any of the subsystems to the input from the bus 78 the operation of each subsystem can be diagnosed and verified.

In summary, diagnostic memory/processor 76 and buses 72 and 78 provide the following capabilities:

A. Provision of "test" information to any component of the system and monitoring of the modifications performed on the "test" information as the "test" proceeds from that component of the system downstream.

B. Comparison of a first representation of visual information received by a first component of the inspection system to a second representation of that visual information outputted by the first component of the inspection system or by any component of the inspection system downstream of the first component.

A particular feature of the diagnostic process described above is that the diagnosis takes place under conditions (timing, processing rate, control) substantially identical to those prevailing when the inspection system is operating in an inspection mode, It is a particular feature of the embodiment of FIG. 1 that the inspection system provides synergism between first apparatus for providing a first output indication of differences between the inspected object and the reference and second apparatus for automatically carrying out a second inspection of at least some areas of the inspected object, thereby to complement the first apparatus by completing said partial output indication of differences provided by said first apparatus. This synergism is provided at least between the binary defect detector 32 and the gray defect detector 64, and also between the initial processing unit, comprising both detectors 32 and 64, and the post-processing unit 67 (see FIG. 13) associated with real time defect recorder 66.

The advantage of providing two-part synergistic inspection of the object, or, more generally, of providing an inspection system having a synergistic plurality of mutually complementing inspection subsystems, as opposed to providing a single inspection system, is that each subsystem of the inspection system may be optimized for a particular requirement of the system as a whole. For example, binary defect detector 32 may "specialize in", or be constructed to be generally optimal for, detection of relatively large defects, without compromising the quality and efficiency of detection of relatively small defects. Gray detector 64 may "specialize in", of be constructed to be optimal for, detection of relatively small defects, without compromising the quality and efficiency of detection of relatively large defects.

Another example of the "specialization" property is that the scanning and subsequent processing provided by real time defect detectors 32 and 64 may be carried out as rapidly as desired, e.g. by decreasing the magnification at which the inspected object is inspected. This need not substantially decrease the quality of detection since the post-processing unit 67 specializes in accuracy at the expense of speed. Preferably, the post-processing unit 67 is operative to increase or decrease its accuracy in accordance with decreased or increased accuracy at which the scanning is being carried out.

Reference is now made to FIGS. 2A–2F which conceptually illustrate a preferred algorithm for the binary defect detector 32 of FIG. 1. The particular example illustrated in FIGS. 2A–2F is that of a 3 pixel×3 pixel neighborhood, it being understood that this example is not intended to be limiting and is provided merely in order to facilitate understanding.

FIG. 2A illustrates corresponding locations of the reference and of the inspected object, on the left and on the right of FIG. 2A respectively. The two locations illustrated differ in that the middle pixel is shaded in the reference and not in the inspected object. Such a difference may either be a genuine defect or a false alarm, due to any of a variety of inaccuracies such as local misregistration and electrical noise. FIG. 2B illustrates binary representations R and I of the above corresponding locations of the reference and the inspected object, respectively.

The binary defect detector 32 of FIG. 1 is operative to detect differences between the binary representation of the reference and the inspected objects. Relatively small detected defects are then preferably categorized as false alarms and filtered out and "eroded", since very small genuine defects are substantially harmless in most applications. The defects which remain after the filtering stage are reported as genuine defects.

The operation of the binary defect detector 32, therefore, preferably comprises two sequential operations:

a. DIFF: identify differences; and b. EROSION: erode false alarms.

These two operators are known in the art and are discussed in detail in image processing texts such as "Digital Picture Processing" by A. Rosenfeld and A. Kak, Academic Press, 1982, the disclosure of which is incorporated herein by reference.

An explanation of the operation of these two operators is now provided, with reference to FIGS. 2B–2F.

The DIFF operator, operating on a particular pair of corresponding binary pixels in the representations of the reference and inspected object, is defined as a function of R and of I.

Sample formulae for DIFF are:

$$DIFF = R \times (-I)$$

or $$DIFF = I \times (-R)$$

or $$DIFF = R \times (-I) + I \times (-R),$$

where ×, + and − denote logical AND, OR and NOT operators, respectively. The first two DIFF operators are subtraction logical operators, and the third DIFF operator is a XOR logical operator. (−R) and (−I) are illustrated in FIG. 2C.

Results of the above three alternative DIFF operators are seen in FIGS. 2D, 2E and 2F, respectively.

"False alarm" differences between binary representations may result from noise in the process of generating the representations. The amount of noise may vary as a function of the neighborhood of the current pixel. For example, the noise in the vicinity of corners is generally larger than the noise in the vicinity of straight edges. Therefore, the cut-off size differentiating genuine defects from false alarms is preferably controllable or selectable either automatically or by the user. Selectability of the cut-off size may be implemented by providing a plurality of EROSION operators, some combination of which may be selected either automatically or by the user. Selection is generally determined as a function of the geometry of the reticle and of a desired ratio between the genuine defects and false alarms. Sample formulae for EROSION operators are:

$$E4S = P0 \times P1 \times P3 \times P5 \times P7 \qquad \text{A.}$$

$$E4A = P0 \times P1 \times P3 \qquad \text{B.}$$

$$E8S = P0 \times P1 \times P2 \times P3 \times P4 \times P5 \times P6 \times P7 \times P8 \qquad \text{C.}$$

$$E8A = P0 \times P1 \times P2 \times P3 \qquad \text{D.}$$

These formulae will be understood with reference to FIG. 3A, which illustrates a binary pixel P0 on which the EROSION operator is centered and the pixel's 5×5 neighborhood, comprising pixels P1 to P24 as shown.

Formula A is a symmetric single step 4-connected operator which erodes the entire perimeter of a binary shape, such as that illustrated in FIG. 3B, thereby reducing its thickness by two pixels, as shown in FIG. 3C. Formula B is an asymmetric single step 4-connected operator which erodes only two sides of the perimeter of a binary shape, thereby reducing its thickness by one pixel. Formula C is a symmetric single step 8-connected operator which erodes the entire perimeter of a binary shape. Formula D is an asymmetric single step 8-connected operator which erodes only two sides of the perimeter of a binary shape.

Each of the single step operators A–D takes into account only those pixels which are directly adjacent to P0 and therefore erode only one pixel from the relevant sides of the perimeter of the binary shape. Analogous operators which take into account two "layers" of pixels P0 to P24 are termed double step operators since they erode two pixels from relevant sides of the perimeter.

A filtering method which may be used as an alternative to the EROSION operator method described above will now be described.

In this method an "acceptance zone" is defined around the edges of the pattern of the reference. Differences which are completely contained within the acceptance zone are classified as false alarms. Differences which fall at least partially outside the acceptance zone are classified as genuine defects. The operator which implements this method is termed the ACCEPTANCE operator.

The acceptance zone comprises two subzones, the first "internal" subzone falling inside the binary shape and the second "external" subzone being disposed externally and adjacent to the binary shape. An internal acceptance subzone of size d comprises the set of pixels eroded from the binary shape by applying a single step EROSION operator d times.

An external acceptance zone of size d is formed by the pixels added to the binary shape when a number d of single step DILATION operators are applied. DILATION operators are known in the art and are discussed in image processing texts such as Digital Picture Processing by A. Rosenfeld and A. Kak, Academic Press, 1982, the disclosure of which is incorporated by reference. Sample formulae for the DILATION operator, with reference to the notation introduced in FIG. 3A, are:

$$D4S = P0 + P1 + P3 + P5 + P7 \qquad 1.$$

$$D8S = P0 + P1 + P2 + P3 + P4 + P5 + P6 + P7 + P8 \qquad 2.$$

The first formula represents a single step 4-connected DILATION operator whereas the second formula represents a single step 8-connected DILATION operator.

The value d may be a constant related to the minimal size of defects or it may vary as a function of the patterns formed by the binary representations of the references.

Figure 4A:
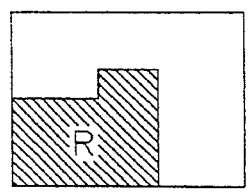
FIGS. 4A–4I are conceptual illustrations of a noise filtering method useful in conjunction with the binary defect detector 32 of FIG. 1.
Figure 4B:
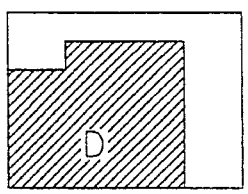
Figure 4C:
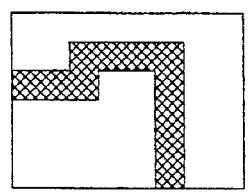
Figure 4D:
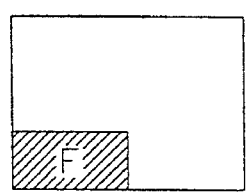
Figure 4E:
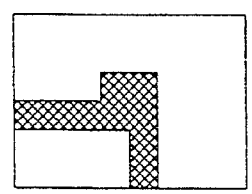

A preferred implementation of the "acceptance zone" method will now be described, with reference to FIGS. 4A–4I. The shaded portion of FIG. 4A illustrates the binary shape R of a portion of the reference. The shaded portion of FIG. 4B illustrates the area D of the reference defined by "adding" R to an external acceptance subzone of R. The shaded portion E of FIG. 4C illustrates the external acceptance subzone of R. The shaded portion of FIG. 4D illustrates F, the area remaining after the erosion operation. The shaded portion of FIG. 4E illustrates the first, internal subzone G of R.

Figure 4F:
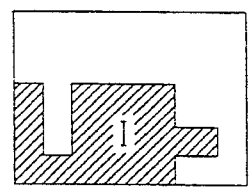
Figure 4G:
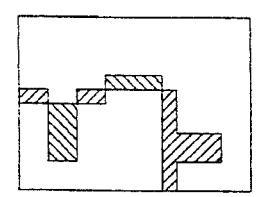
Figure 4H:
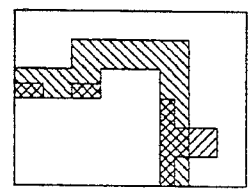
Figure 4I:
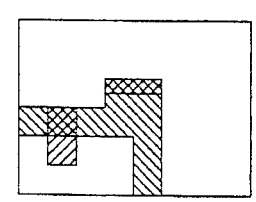

The shaded portion of FIG. 4F illustrates the binary shape I of a portion of the inspected object corresponding to R. FIG. 4G illustrates the difference between the I shape and the R shape. The difference is operationalized as I–R and as R–I, as shown. FIGS. 4H and 4I illustrate the ACCEPTANCE operator. FIG. 4H shows the subtraction of external zone E from I–R resulting in a "false alarm" zone H and a "true defect" zone J. FIG. 4I shows the subtraction of internal zone G from R–I resulting in a "false alarm" zone K and a "true defect" zone L.

Figure 5:
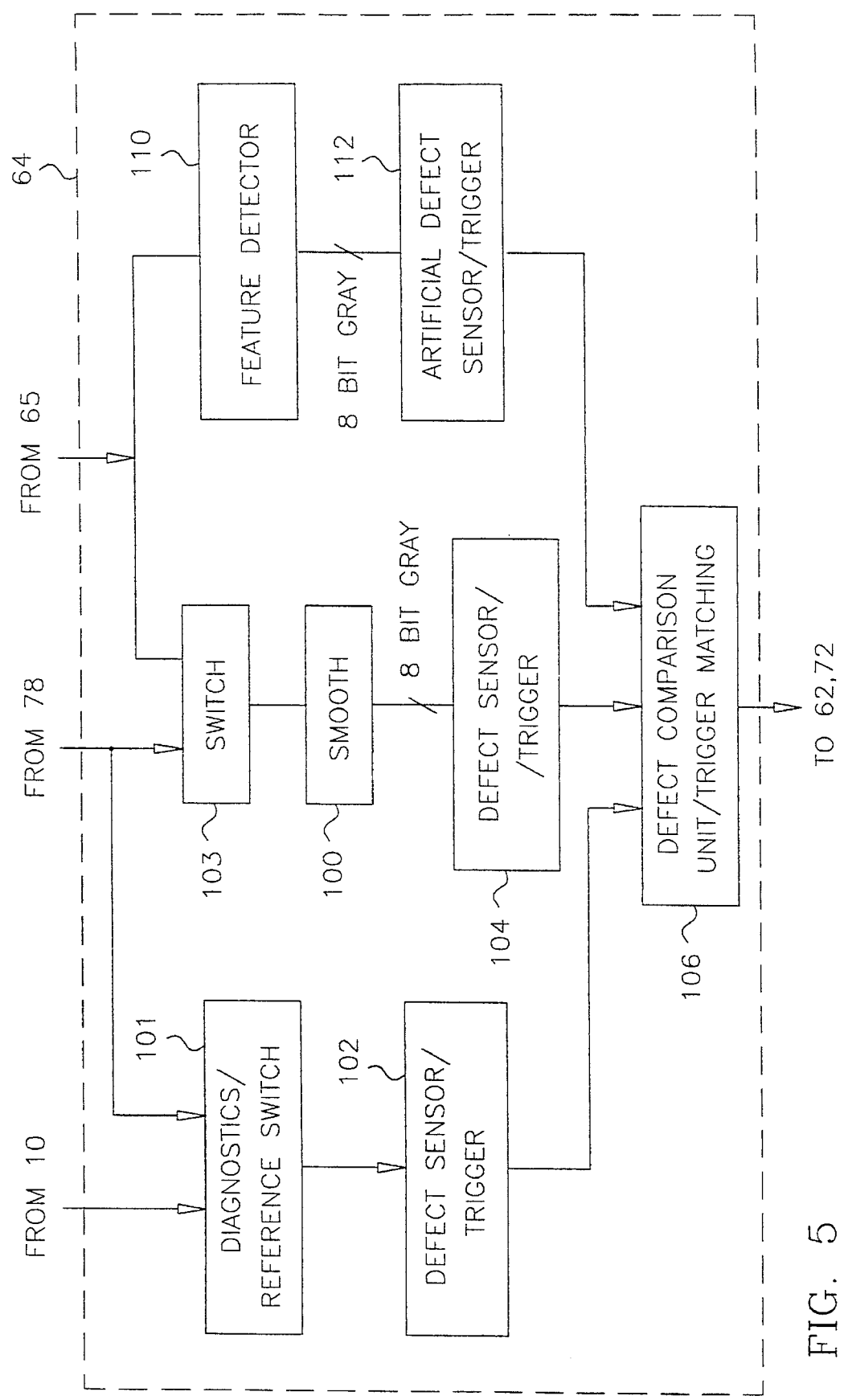
FIG. 5 is a block diagram of the ultra fine level defect detection unit 64 of FIG. 1.

Reference is now made to FIG. 5 which illustrates the ultra fine level defect detection unit 64 of FIG. 1.

The detection processes in both the inspected channel and the reference channel, and the process of comparing the two channels all employ full 8 bit gray level information. The processes are preferably based on multipixel operators called "triggers", described in greater detail hereinbelow, that are sensitive to specific variations in energy between a pixel and its surrounding pixels (energy gradients) and have the added important feature of being only triggered by small defects.

As shown, the ultra fine level defect detector 64 typically receives 8 bit gray level information representing the object to be inspected from the scanner 10. Defect detector 64 also receives reference information via switch 65 comprising either aligned binary rasterized information from database alignment memory 59, or aligned gray information from die alignment memory 60. A switch 103 is provided for selecting which of the above two types of information is to be provided. Switch 103 is also operative to allow a diagnostic mode or an inspection mode to be selected.

A smoothing unit 100 is preferably provided to convert the binary information from database alignment memory 59 to 8 bit gray level information, thereby to enable its comparison with the 8 bit gray level information representing the inspected object. If the information arriving at smoothing unit 100 is gray information from die alignment memory 60, switch 103 issues a suitable command to smoothing unit 100 in order to prevent smoothing of the information.

The gray level information representing the inspected object and reference respectively is provided via a switch 101 and smoothing unit 100 respectively, to defect sensing elements 102 and 104 respectively. Switch 101 is operative to allow a diagnostic mode or an inspection mode to be selected. In the first instance, the gray level information provided to defect sensing element 102 is provided by test bus 78 (FIG. 1). In the second instance, the gray level information provided to defect sensing element 102 is provided by scanner 10 (FIG. 1).

Defect sensing elements 102 and 104 are preferably substantially identical and are based upon a plurality of defect detection operators also called triggers, described in detail hereinbelow.

Defect sensing element 102 is operative to sense inspected object location representations which correspond to putative defects in the inspected object. However, the triggers may also react to some legitimate geometries, thereby causing unwanted false alarms. In order to reduce these false alarms, defect sensor 104 is provided which applies the same triggers to the reference information. The legitimate geometries that prompt the trigger in the datastream of the inspected object do the same in the reference stream.

A defect comparison unit 106 compares triggers originating in defect sensor 102 to triggers originating in defect sensor 104 and in artificial defect sensor 112 (see below). Typically, defect comparison unit 106 generates an output indication of each location of the inspected object which triggers defect sensor 102 and for which it is true that no trigger was generated by either defect sensor 104 or artificial defect sensor 112 in a window of predetermined size around the same location in the reference. A typical window size is 5×5 pixels. According to one embodiment, identified defects are only discarded if the trigger generated by defect sensor 104 and/or artificial defect sensor 112 indicates a putative defect along the same direction, having the same polarity (i.e. both sensors identify the defect as a "hill" or as a "valley"), and having a similar TDE value as the putative defect to be discarded. The term "TDE" is defined below.

Reference is now made to FIGS. 6A–6L which illustrate a plurality of triggers which may be employed by defect sensors 102 and 104 of ultra fine level defect detector 64. Each trigger is superimposed onto a 4×4 pixel neighborhood (A–D, 0–3). The shaded areas depict chrome-bearing or opaque areas of the reticle.

The plurality of defect sensing triggers comprises the following triggers i–viii:

i. A narrow vertical operator, whose dimensions are typically 4×1 pixels, and which is shown by a heavy line in FIG. 6A. This operator is particularly useful in detecting hill or valley defects of the types illustrated in FIGS. 6A, 6B and 6L.

ii. A wide vertical operator, whose dimensions are typically 4×2 pixels, and which is shown by a heavy line in FIG. 6C. This operator is particularly useful in detecting hill or valley defects of the types illustrated in FIGS. 6C and 6D.

iii. A narrow horizontal operator, whose dimensions are typically 1×4 pixels, and which is shown by a heavy line in FIG. 6E. This operator is particularly useful in detecting hill or valley defects of the types illustrated in FIGS. 6E, 6J and 6L.

iv. A wide horizontal operator, whose dimensions are typically 2×4 pixels, and which is shown by a heavy line in FIG. 6F. This operator is particularly useful in detecting hill or valley defects of the types illustrated in FIGS. 6D and 6F.

v. A wide forward slant diagonal operator, a typical configuration of which is shown by a heavy line in FIG. 6G. This operator is particularly useful in detecting hill or valley defects of the types illustrated in FIGS. 6D and 6G.

vi. A wide backward slant diagonal operator, a typical configuration of which is shown by a heavy line in FIG. 6H. This operator is particularly useful in detecting hill or valley defects of the types illustrated in FIGS. 6D and 6H.

vii. A narrow forward slant diagonal operator, a typical configuration of which is shown by a heavy line in FIG. 6I. This operator is particularly useful in detecting hill or valley defects of the types illustrated in FIGS. 6D and 6I.

viii. A narrow backward slant diagonal operator, a typical configuration of which is shown by a heavy line in FIG. 6K. This operator is particularly useful in detecting hill or valley defects of the types illustrated in FIGS. 6D, 6K and 6L.

It is noted that an operator useful in detecting a particular defect is also useful in detecting a corresponding defect in which each dark area is replaced with a light area and each light area is replaced with a dark area.

A central area and two peripheral areas are defined for each of the eight operators described above. The respective central areas for each of the eight operators respectively comprise the following pixels, with reference to the grid notation defined by the row-defining letters and column-defining numbers in FIGS. 6A, 6C, 6E, 6F, 6G, 6H, 6I and 6K respectively:

i. B2, C2
ii. B1, B2, C1, C2
iii. C1, C2
iv. B1, B2, C1, C2
v. B1, B2, C1, C2
vi. B1, B2, C1, C2
vii. B2, C1
viii. B1, C2

The first and second peripheral areas for each of the eight operators respectively comprise the following pixels, with reference to the grid notation defined by the row-defining letters and column-defining numbers in FIGS. 6A, 6C, 6E, 6F, 6O, 6H, 6I and 6K respectively:

|      | First        | Second       |
|------|--------------|--------------|
| i.   | A2           | D2           |
| ii.  | A1, A2       | D1, D2       |
| iii. | C0           | C3           |
| iv.  | B0, C0       | B3, C3       |
| v.   | A2, A3, B3   | C0, D0, D1   |
| vi.  | A0, A1, B0   | C3, D2, D3   |
| vii. | D0           | A3           |
| viii.| A0           | D3           |

Figure 6A:
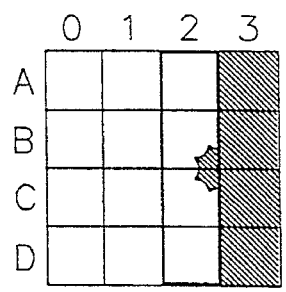
FIGS. 6A–6L are conceptual illustrations of types of defects and defect sensing operators used in a preferred embodiment of the ultra fine level defect detection unit 64 of FIG. 1.
Figure 6B:
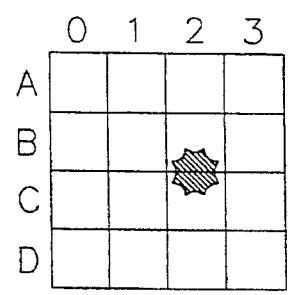
Figure 6C:
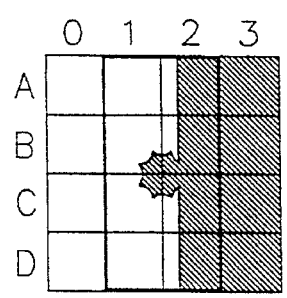
Figure 6D:
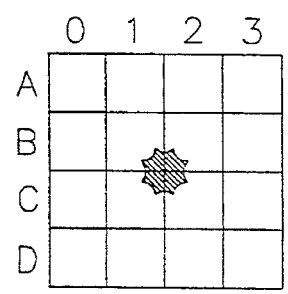
Figure 6E:
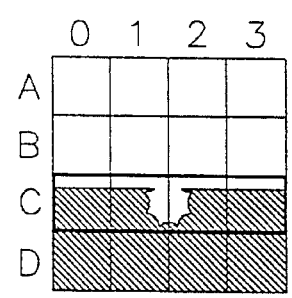
Figure 6F:
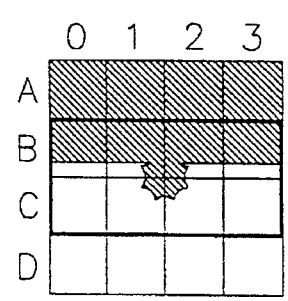
Figure 6G:
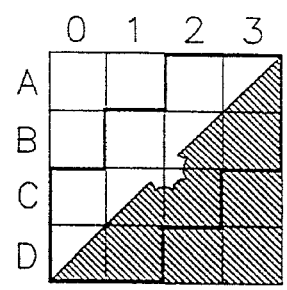
Figure 6H:
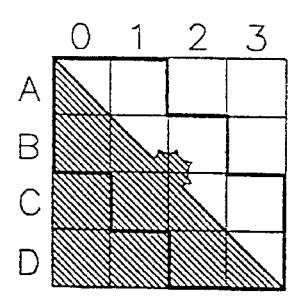
Figure 6I:
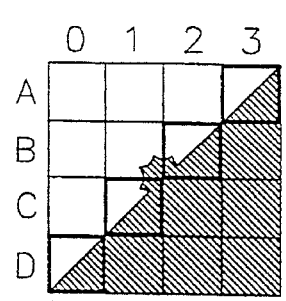
Figure 6J:
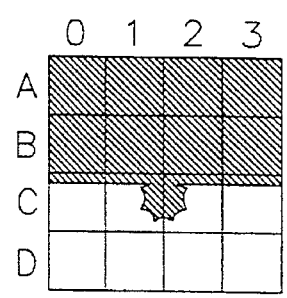
Figure 6K:
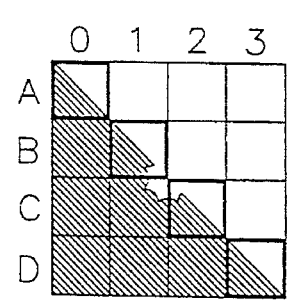
Figure 6L:
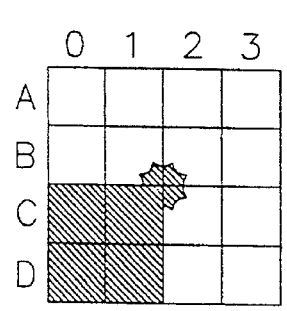

For each operator, the sum of the energy levels of the central area pixels is denoted C. For example, for operator i, C=B2+C2. A weighted or unweighted sum of the energy levels of the pixels in the first periphery is denoted as P1. For example, for operator i, P1=A2. However, a preferred formula for operator V shown in FIG. 6G is the weighted sum: P1=A2+2A3+B3.

A weighted or unweighted sum of the energy levels of the pixels in the second periphery is denoted as P2. For example, for operator i, P2=D2. However, a preferred formula for operator shown in FIG. 6G is the weighted sum: P2=C0+2D0+D1.

Defects are detected by comparing the sum of energy levels of the center pixels of an operator to the sum (weighted or simple) of energy levels of each of the peripheries. If the sum of energy at the center deviates by more than a certain threshold value T from the sums of energies of the peripheries, a defect, residing in the central area, is identified. The use of a non-zero positive threshold value is preferable since it eliminates misidentification of noise as a defect and also filters out very small defects.

According to one preferred embodiment, the threshold value used in sensor 102 is slightly higher than the threshold value used in sensor 104. Consequently, substantially any putative defect which triggers sensor 102 will also trigger sensor 104, thereby reducing the false alarm rate. An additional or alternative method for ensuring that substantially any nondefective location which triggers the inspected object channel will also trigger the reference channel is provision of the artificial defect detection channel described hereinbelow.

According to a preferred embodiment, for operators i–iv, a hill or a valley defect is identified if the following conditions respectively hold:

valley: C+T<2×P1 and C+T<2×P2 hill: C–T>2×P1 and C–T>2×P2

It is noted that here, the peripheral sums are multiplied by 2 since the peripheral areas are each half as large as the corresponding center area, and consequently are only comparable therewith when the peripheral energy levels are doubled.

For operators v–viii, a hill or a valley defect is identified if the following conditions respectively hold:

valley: C+T<P1 and C+T<P2 hill: C–T>P1 and C–T>P2

A sample computation for operator iv disposed at pixels B0–B3 and C0–C3 of FIG. 60, assuming the defect of FIG. 6D has a gray value of 0 and an area of 0.5 pixel which is equally distributed over the four white (gray level=255) pixels B1, B2, C2 and C3, is as follows:

$B1=B2=C2=C3=\frac{7}{8}\times 255=$ approximately 225;

$C=900$;

$2\times P1=2(A1+B1)=2(255+255)=1020$;

$2\times P2=2(A4+B4)=2(255+255)=1020$.

The size of the defect may be quantified, if desired, by defining a quantity designated as the Total Delta Energy (TDE). For each of the operators, the TDE is defined as the total energy of the central pixels minus the sum of the energies of both peripheries. By comparing the TDE to three different thresholds, detected defects may be classified as small, medium or large.

A relatively large defect does not result in formation of a valley profile and the operator is not "triggered" thereby. Single edges also do not result in formation of valley or hill type profiles. A double edged profile also does not trigger the operator if the ratio of the size of the operator to the width of the profile is sufficiently small.

In order to detect a defect disposed on the edge of, for example, a vertically disposed pattern, inspection along a vertical axis is preferable, whereas a defect disposed on the edge of a horizontally disposed pattern is most easily detected by inspection along a horizontal axis. Preferably, therefore, defect sensors 102 and 104 operate on each location to be inspected along a plurality of axes, such as four axes separated from one another by 45 degrees (termed the vertical axis, the horizontal axis, the 45 degree axis and the 135 degree axis). Therefore, each defect may be characterized as lying along a particular axis or axes. A defect may also be characterized as either a valley or excess chrome defect (such as a pin-dot as illustrated in FIGS. 6B and 6D) or a hill or deficient chrome defect (such as a pin-hole), depending on the shape of the detected energy profile. A generally point-symmetric defect, such as a pin hole or pin dot defect, will generally be detected along all detection axes.

A defect sensing operator of one of the types i–viii described above may also be expected to be triggered by certain legitimate (non-defective) features of the inspected object representation operated upon. For example, a geometry such as a a corner of less than 135 degrees may trigger the defect sensor.

This situation is partially remedied by providing a reference detection channel parallel to the inspected object detection channel and substantially identical thereto, as explained above. However, referring again to FIG. 5, it may sometimes occur that defect sensor 102 is triggered by a non-defective location in the representation of the inspected object but the identical (due to the non-defectiveness) location in the representation of the reference does not succeed in triggering defect sensor 104. This situation may occur even if defect sensors 102 and 104 are identically constructed, because the two sensors may not receive exactly the same input, due to the fact that the inputs thereto may not be identically generated. For example, the input to sensor 102 of FIG. 5 may be generated by scanner 10, which scans in 8 bit depth, whereas the input to sensor 104 of FIG. 5 may be generated by converting binary database information to 8 bit level. Also, even a "defectless" object to be inspected does not exactly correspond to its database precursor, because, inter alia, corners of the database pattern tend to be rounded as an artifact of the process whereby the inspected object is created.

Consequently, a preferred remedy is to provide a reference detection channel parallel to defect sensor 104 and comprising a feature detector lid as well as an artificial defect sensor 112. The artificial defect detection channel may be designed on an ad-hoc basis to ensure that substantially any legitimate configuration which is misidentified by defect sensor 102 as a defect in the inspected object and which does not also trigger defect sensor 104, will cause a trigger along the artificial defect detection channel, thereby to allow the putative defect to be categorized as a false alarm.

The feature detector 110 is also termed herein "the MIC feature detector", abbreviated as "FDM". The FDM is designed to recognize predefined geometric configurations in the reference stream. The predefined configurations include those which generate a valid trigger in the inspected object but not in the reference. For those configurations, the FDM creates an artificial trigger that is added to the stream of triggers produced by the reference.

Generally, the FDM performs a template matching operation in which the templates are the predefined configurations and the search area is the stream of the reference. Since the size of the template is preferably large, such as 8×8 bits, a single look-up table may not be practical. Instead, several LUTs may be combined into a decision tree. The structure of the decision tree is based on the fact that the number of templates to be recognized is small with respect to the number of binary combinations of 8×8 bits. A preferred embodiment of feature detector 110 is described in Appendix 4.

Figure 7A:
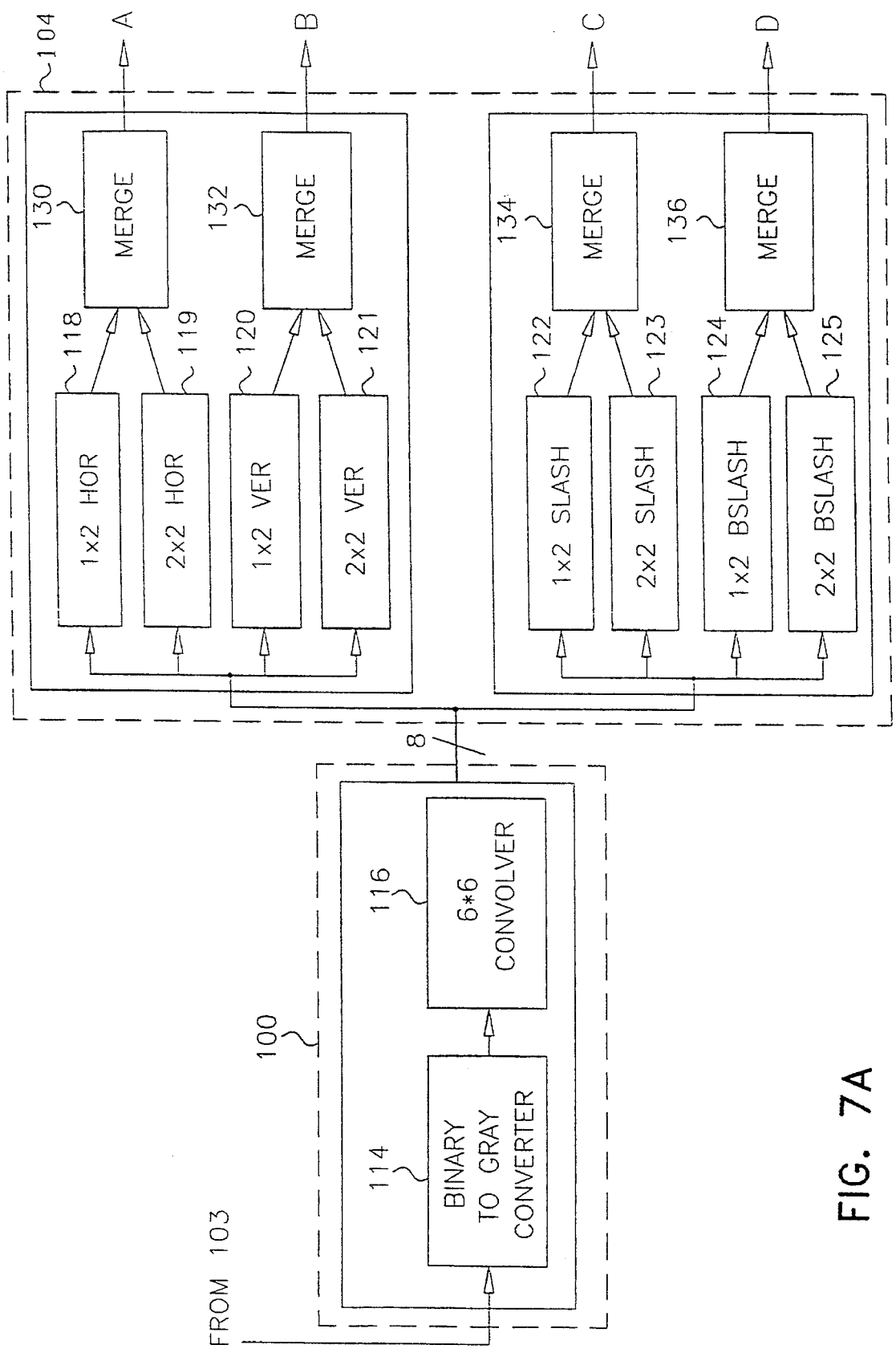
FIGS. 7/1 and 7/2 are, composed of FIGS. 7A and 7B, block diagrams of smoothing unit 100, defect detectors 102 and 104 and defect comparison unit 106 of FIG. 5.
Figure 7B:
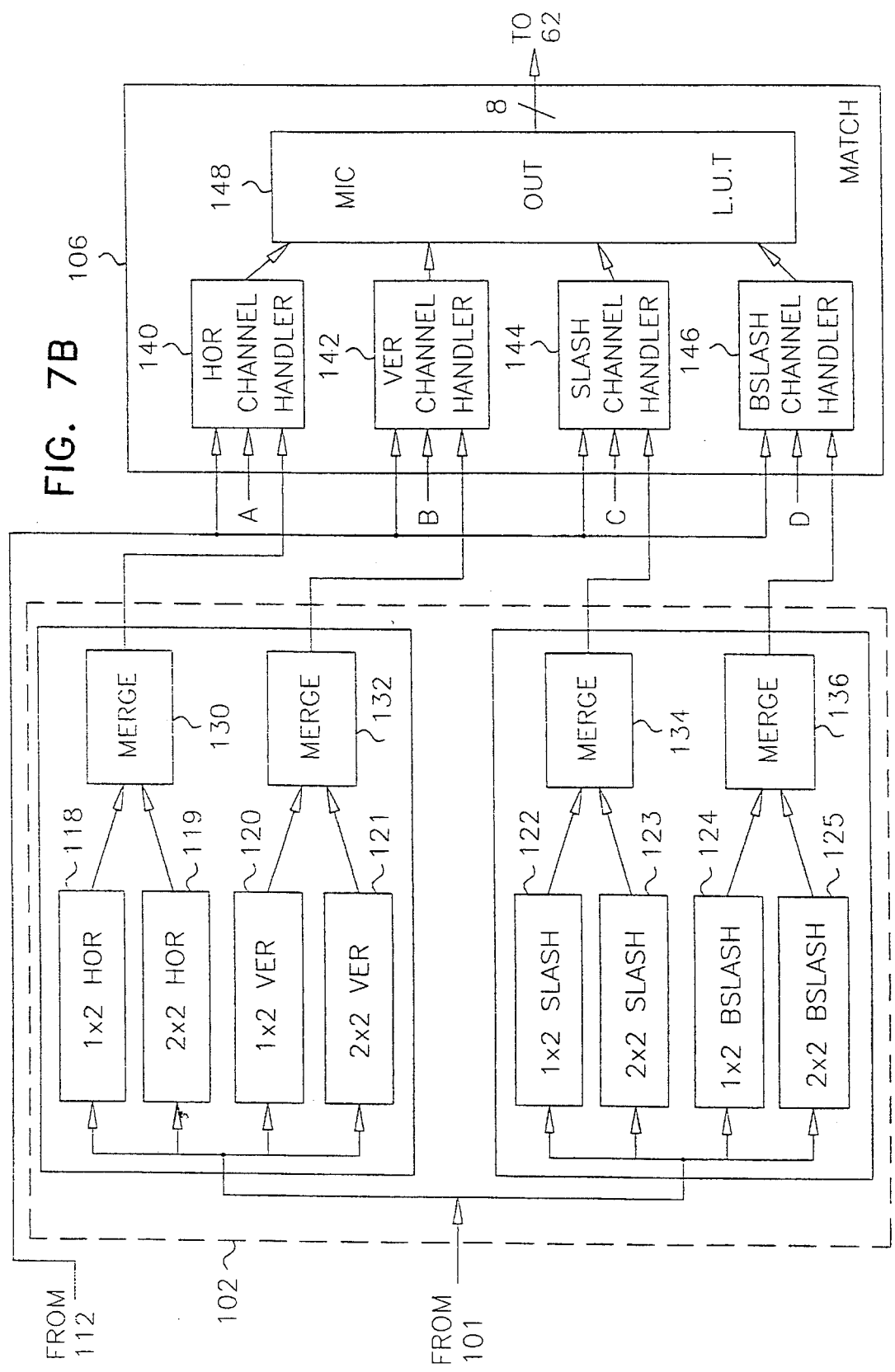

FIG. 7, composed of FIGS. 7A and 7B, is an intermediate level block diagram of smoothing unit 100, defect detectors 102 and 104 and defect comparison unit 106 of FIG. 5.

As shown, smoothing unit 100 preferably comprises a binary-level to gray-level converter 114 and a convolving unit 116. Binary to gray converter 114 converts the database information which is provided in binary format at high resolution format into low resolution (such as 8 bit) gray level information, using any suitable method such as binary pixel counting. Convolver 116 further increases the number of shades of gray and provides spatial smoothing of the information by convolving the database information (DB) with a smoothing two-dimensional function, using a Gaussian or any other suitable function.

A preferred implementation of such a function is a 5×5 pixel template T such as $$T = 1/48 \times M \text{ where } M = \begin{matrix} 1 & 1 & 1 & 1 & 1 \\ 1 & 2 & 4 & 2 & 1 \\ 1 & 4 & 8 & 4 & 1 \\ 1 & 2 & 4 & 2 & 1 \\ 1 & 1 & 1 & 1 & 1 \end{matrix}$$

The convolution is carried out by multiplying each pixel and its 5×5 surrounding neighborhood within the database by the template as follows:

Sum $[(DB)_{ij} (T)_{ij}]$ $i,j=1, \ldots, 5$

Convolver 116 may also be a 6×6 convolver or may have any other suitable dimension.

Defect detector 102 comprises a plurality of defect detection operator units, preferably eight defect detection operator units 118, 119, 120, 121, 122, 123, 124 and 125 connected in parallel. The eight defect detection operator units may be based on the defect detection operators i–viii described hereinabove. Specifically, defect detection operator units 118, 119, 120, 121, 122, 123, 124 and 125 correspond to operators iii, iv, i, ii, vii, v, viii and vi, respectively. Each defect detection operator unit is operative to span the stream of the input pixel to a required template and then mark "suspect" areas as triggers.

Indications of horizontally oriented defects are provided by defect detection operator units 118 and 119 and are merged by a merging unit 130. Indications of vertically oriented defects are provided by defect detection operator units 120 and 121 and are merged by a merging unit 132. Indications of forward slanting diagonally oriented defects are provided by defect detection operator units 122 and 123 and are merged by a merging unit 134. Indications of backward slanting diagonally oriented defects are provided by defect detection operator units 124 and 125 and are merged by a merging unit 136.

As shown, defect detector 104 may be substantially identical to defect detector 102, apart from run time parameters and for the parameters of the defect detection operator units.

Defect comparison unit 106 typically comprises a plurality of channel handlers corresponding to a plurality of directions along which the defect inspection process takes place. In the shown embodiment, four channel handlers 140, 142, 144 and 146 are provided which correspond to the horizontal, vertical, forward diagonal and backward diagonal directions, respectively.

The channel handler for each direction receives information about triggered reference locations from artificial defect sensor 112 as well as from the merging unit within defect detector 104 which relates to that direction. This information is compared with the information about triggered inspected object locations arriving from the merging unit within defect detector 102 which relates to that direction. After discarding putative defects which triggered both the inspected and reference channels, as explained above, the plurality of channel handlers provides the information about the remaining defects to a LUT 148. LUT 148 is operative to merge the information regarding defects detected along each of the plurality of directions, such as horizontal, vertical, forward diagonal and backward diagonal directions. LUT 148 may be based upon an OR logical function. The merged information provided by LUT 148 is received by defect processor 62 of FIG. 1.

Reference is now made to FIGS. 8A to 8H which are block diagrams of preferred embodiments of defect detection operator units 118, 119, 120, 121, 122, 123, 124 and 125 respectively. As stated above, each defect detection operator unit is operative to span the stream of the input pixel to a required template and then mark "suspect" areas as triggers. A coordinate system for the 8 templates of the 8 defect detection operator units 118, 119, 120, 121, 122, 123, 124 and 125 was defined above with reference to FIGS. 6E, 6F, 6A, 6C, 6K, 6H, 6I and 6G respectively. The same coordinate system will be employed herein with reference to FIGS. 8A to 8H.

Reference is now made particularly to FIG. 8A which is a block diagram of the narrow horizontal defect detection operator unit 118 which operates on a spanned 1×4 template (C0, C1, C2, C3). An adder 150 computes the central area sum C, defined above with reference to FIGS. 6A–6K, which may be the sum of C1 and C2. The sum of the energies of the peripheries, P1 and P2, defined above with reference to FIGS. 6A–6K is computed by an adder 152. A subtracter 154 subtracts 2×C0, twice the first peripheral sum, from the central area sum C. A subtracter 156 subtracts 2×C3, twice the second peripheral sum, from the central area sum C. LUTs 158 and 160 respectively compare the respective outputs of subtracters 154 and 156 to respective programmable threshold values. A subtracter 162 computes the TDE value, defined above with reference to FIGS. 6A–6K. The TDE value and the comparison results of LUTs 158 and 160, via a logic unit 164, are received by a LUT 166 which provides an output indication of the defect/false alarm status, TDE level and polarity of the defect detected by the narrow horizontal trigger.

Figure 8C:
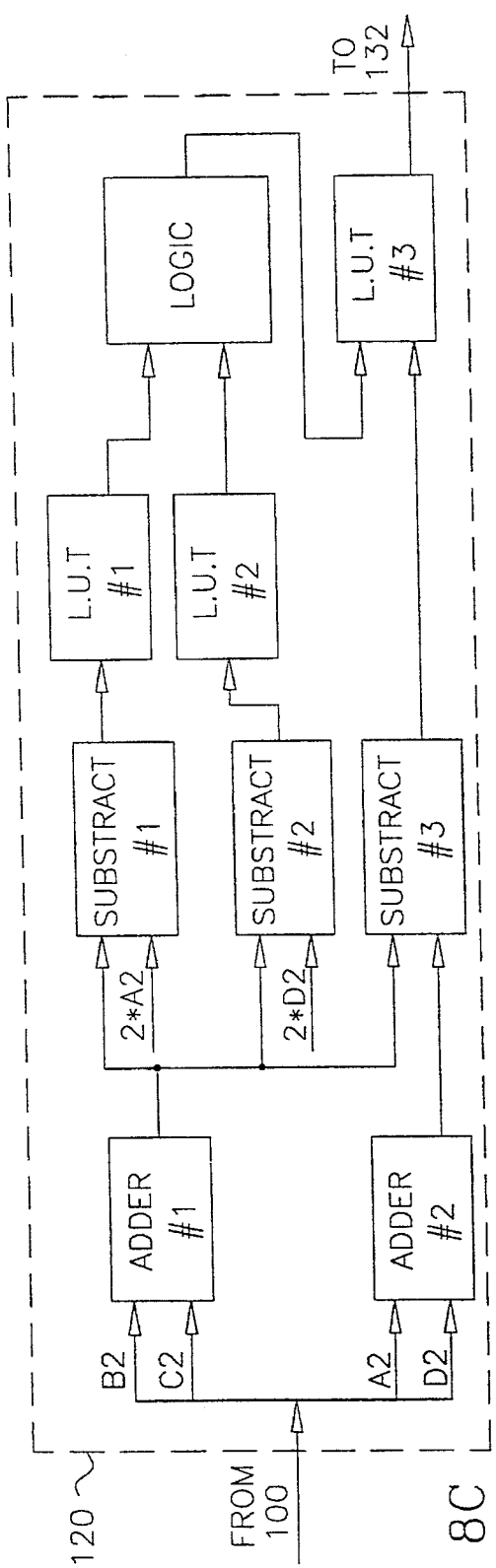
Figure 8D:
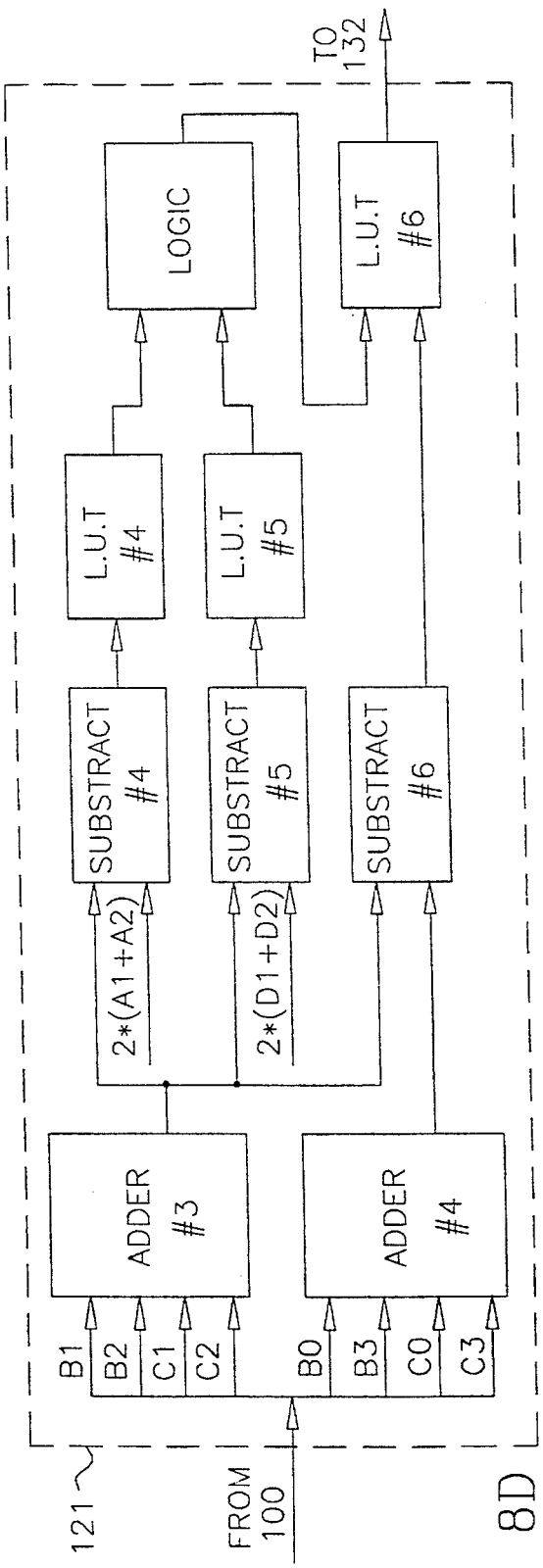
Figure 8E:
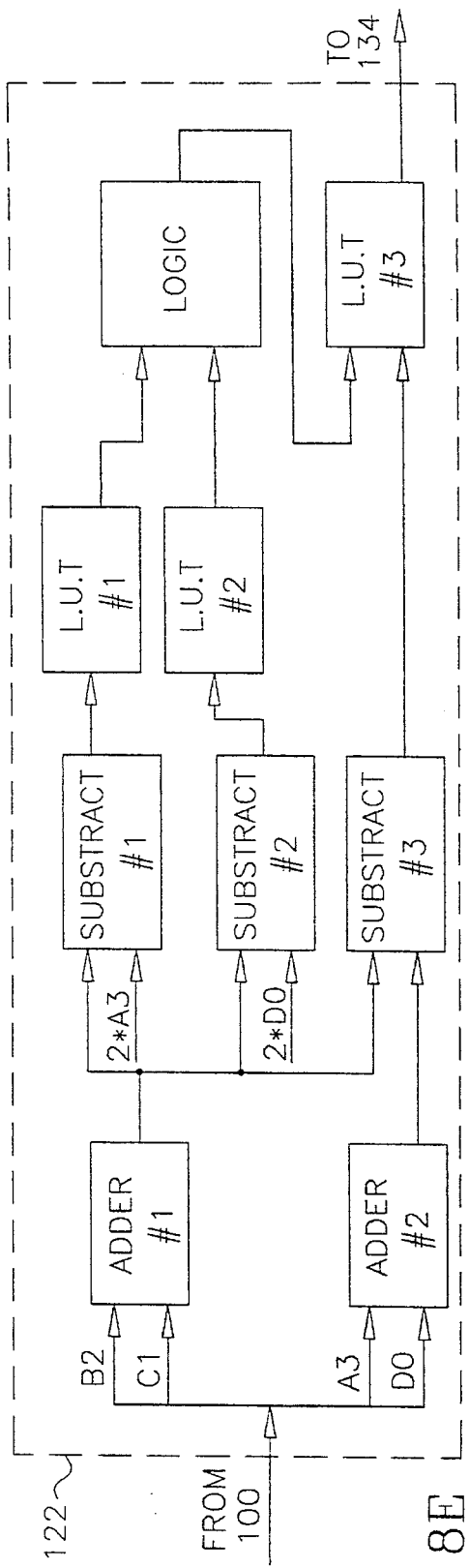
Figure 8F:
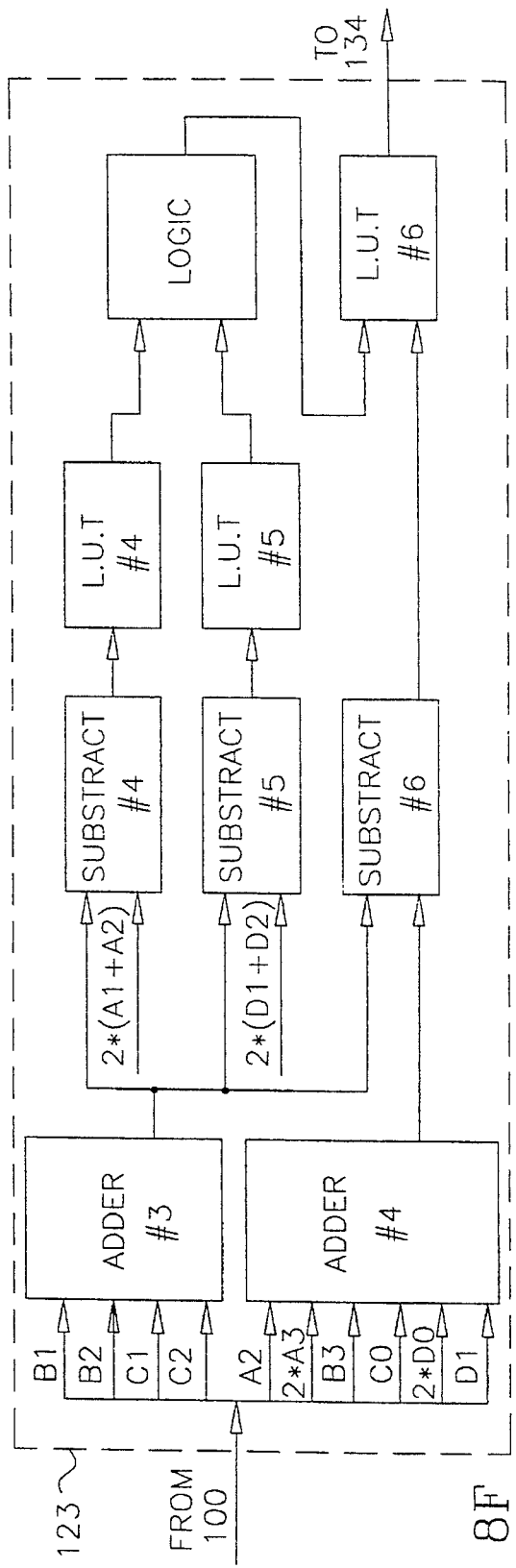

The defect detection operator units of FIGS. 8B to 8H are constructed analogously to the defect detection operator unit of FIG. 8A and therefore will not be discussed in detail for brevity.

Figure 9:
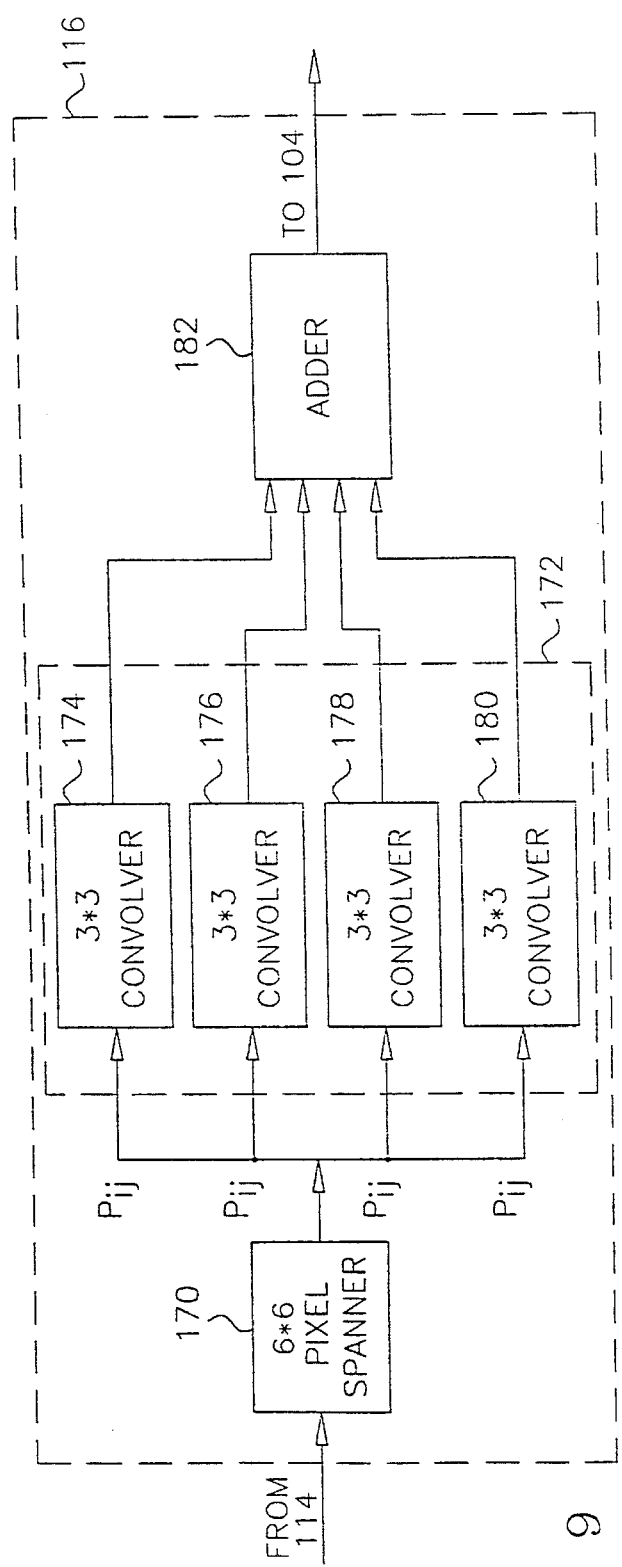
FIG. 9 is a block diagram of convolver 116 of FIG. 7.

Reference is now made to FIG. 9 which is a block diagram of convolver 116 of FIG. 7. The convolver preferably comprises a 6×6 pixel spanner 170 connected to an array 172 of 3×3 convolvers, typically comprising four convolving means 174, 176, 178 and 180.

Figure 10:
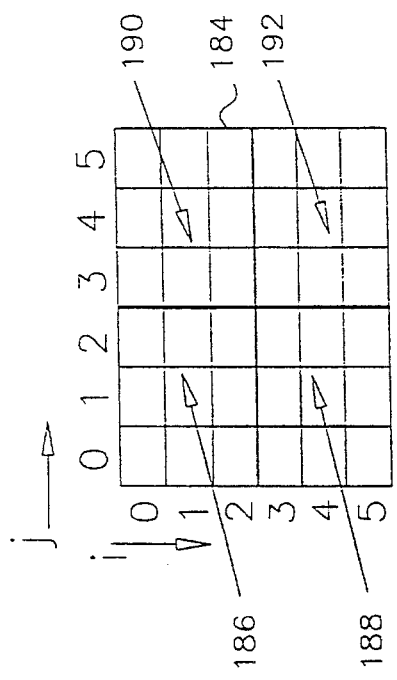
FIG. 10 is an illustration of the coordinates of a window used by convolver 116 of FIG. 7.

After the data resolution is reduced in unit 114 of FIG. 7, the data is spanned to a 6×6 window 184, illustrated in FIG. 10. As seen in FIG. 10, the 6×6 window may be partitioned into four small 3×3 pixel arrays 186, 188, 190 and 192 which drive the convolving means 174, 176, 178 and 180 respectively. The outputs of the four convolver units are summed by an adder 182, thereby to provide an 8 bit gray level output.

Figure 11A:
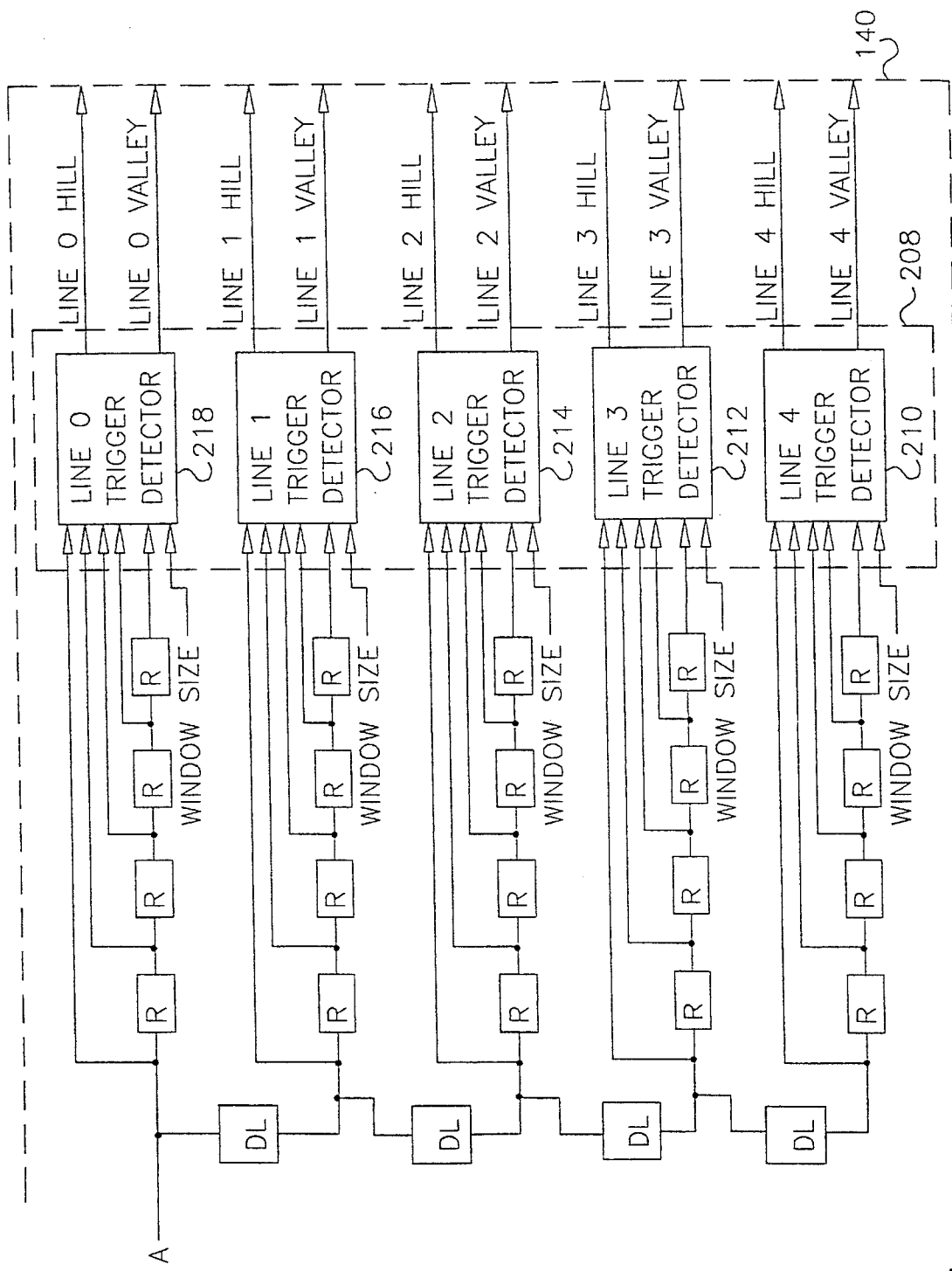
FIGS. 11/1 and 11/2 are, composed of FIGS. 11A and 11B, block diagrams of channel handler 140 of FIG. 7.
Figure 11B:
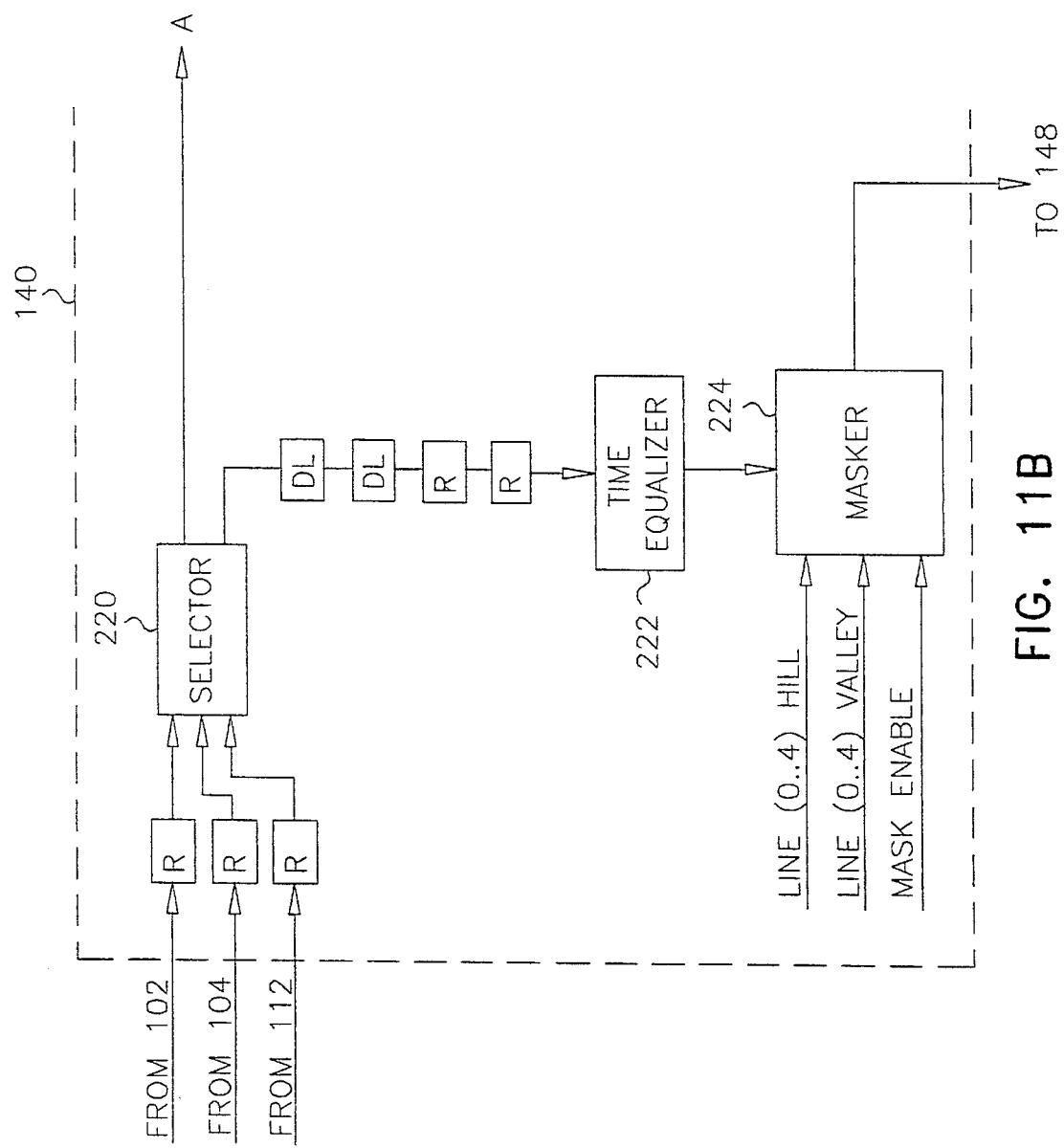

Reference is now made to FIG. 11, composed of FIGS. 11A and 11B, which is a block diagram of a preferred embodiment of channel handler 140 of FIG. 7. Channel handlers 142, 144 and 146 may be identical to channel handler 140.

As seen in FIG. 11, the channel handler 140 receives, in parallel, information regarding the reference from detectors 104 and 112 of FIG. 5, and information regarding the inspected object from detector 102 of FIG. 5. The two channels of reference information are merged by an OR logical function. A spanning operation follows, resulting in a window typically having dimensions of 5×5. Finally, a parallel array 208 of trigger detector units, typically comprising five trigger detector units 210, 212, 214, 216 and 218, searches the window for valid "hill" and "valley" triggers.

The inspected object information channel, arriving from detector 102 of FIG. 2, is directed via a selector 220 to a time equalizing unit 222 which is operative to delay the inspected object data by a fixed time interval. After the delay, the inspected object information is provided to a masking unit 224. Simultaneously, masking unit 224 receives two channels of data from each of the five trigger detector units 210, 212, 214, 216 and 218. The two channels of data are indicative of hill defects and valley defects respectively. Masking unit 224 masks or cancels out putative defects in the inspected object if a trigger, typically a trigger of the same polarity and having a similar TDE value, is contained within the 5×5 window corresponding to the putative defect, as explained above.

In FIG. 11, "DL" indicates a unit which introduces a delay of one line and "R" indicates a unit which introduces a delay of one pixel.

Figure 12:
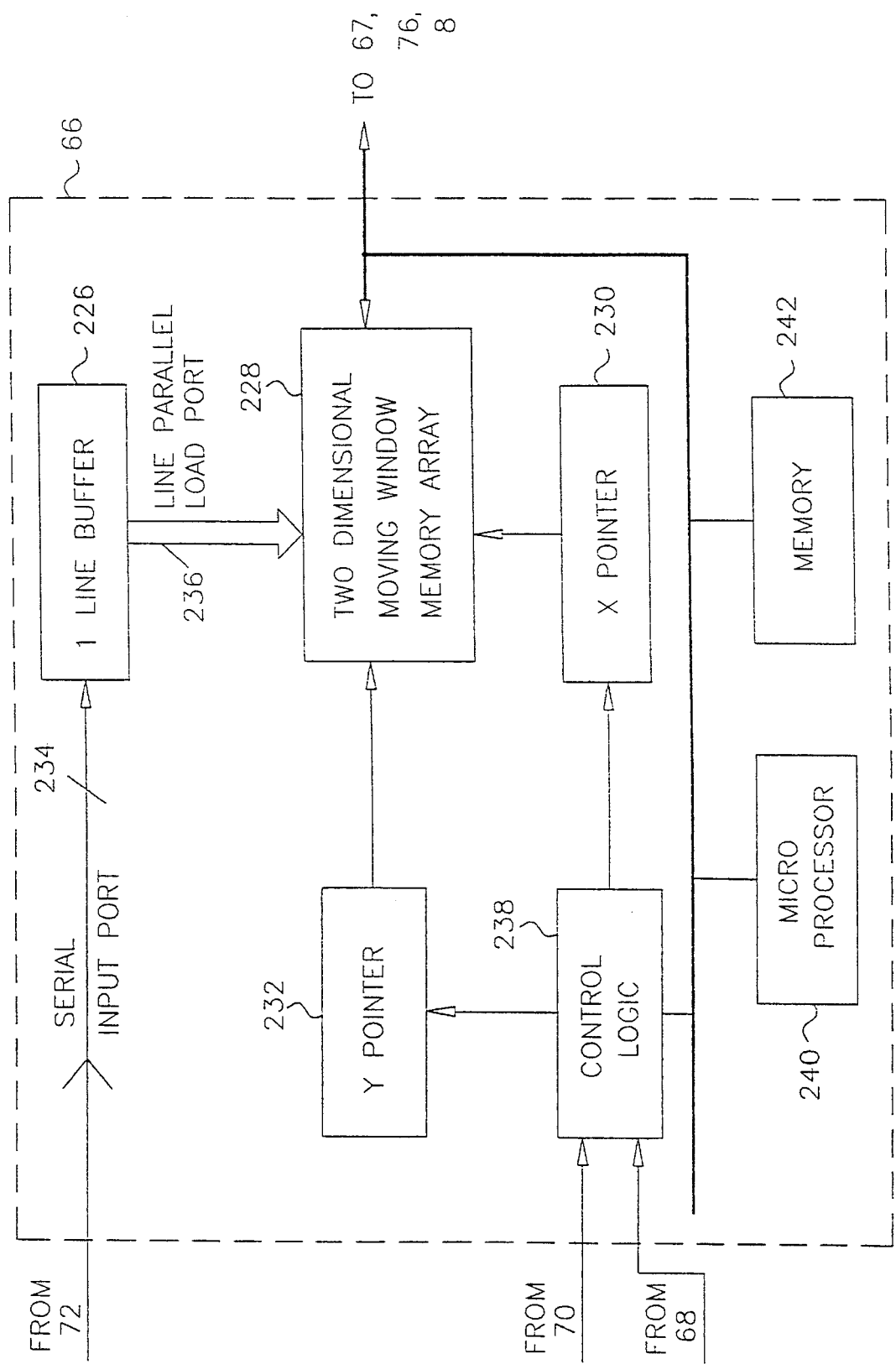
FIG. 12 is a block diagram of the real time defect recording unit 66 of FIG. 1.

Reference is now made to FIG. 12 which is a block diagram of the real time defect recorder 66 of FIG. 1. As seen, unit 66 comprising a line buffer 226, m pixels in length, which interfaces with a memory 228, such as a RAM, accessed by an x pointer 230 and a y pointer 232. Memory 228 typically comprises a 1K×1K two-dimensional array.

The operation of the recording unit 66 is as follows: the line buffer 226 receives, during each line time, a representation of a line of the inspected object or reference from input bus 72 (FIG. 1) via a serial input port 234. Each line is sequentially loaded via a parallel input port 236 onto the memory 228, at the y location pointed at by y pointer 232. Each time a line is loaded onto the memory 228, the y pointer is incremented. Therefore, the memory acts as a moving window storing a selected number of lines, such as 1K, which are the most recently scanned lines of the object.

When a defect occurs, the recording apparatus 66 is alerted to this occurrence by defect processor 62 (FIG. 1). The addresses of a neighborhood of pixels surrounding the defect are computed based on the coordinate signal arriving from defect processor 62 which identifies the location of the defect. The portion of the contents of moving window 228 identified by those addresses is random-access read, using X-Y addressing, by a control logic unit 238, and is supplied to postprocessor 67 (FIG. 1). A processing unit 240 is provided for initialization and testing.

Upon receipt of a trigger and an indication of the location thereof, the recording unit 66 records a representation of a neighborhood of that location, typically 32×24 pixels in size, from image bus 72 (FIG. 1). The representation on image bus 72 may be the representation provided by any one of the components of the system interfacing with the image bus 72, as shown. Controller 8 (FIG. 1) is operative to determine which representations will be loaded onto image bus 72. These representations are then passed on through a temporary memory 242 to postprocessor 67 of FIG. 1 where one or both of the following functions are performed:

(a) determination of whether the putative defect is an actual defect or a false alarm; and (b) diagnosis of the performance of the subsystems of the inspection system which provide these representations, thereby enabling the operation of these elements to be modified in order to reduce the false alarm rate.

Figure 13:
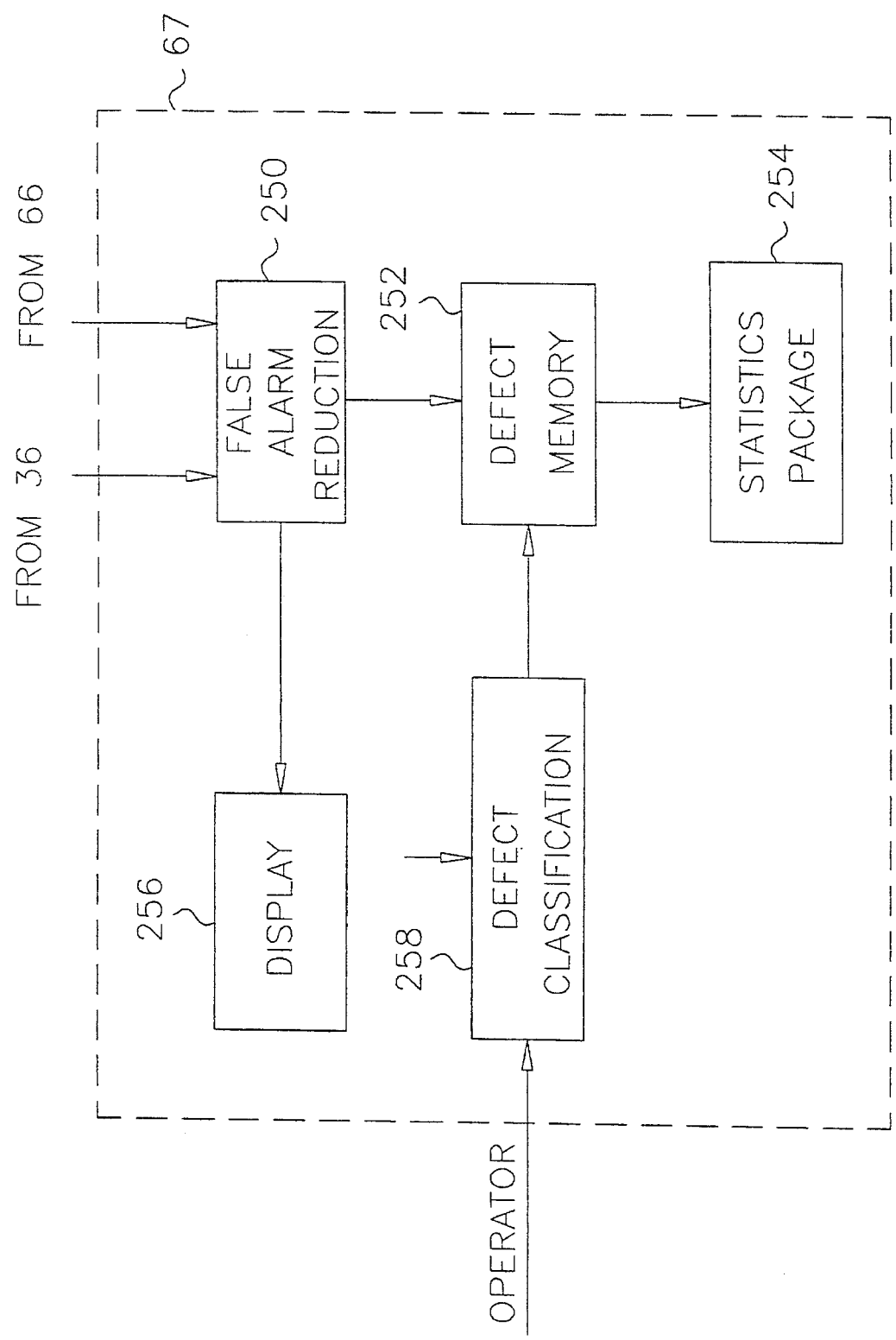
FIG. 13 is a block diagram of the postprocessor 67 of FIG. 1.

Reference is now made to FIG. 13 which is a conceptual illustration of the postprocessor 67 of FIG. 1.

The postprocessor 67 comprises a false alarm rate reducing unit 250 which receives real time recorded representations of a plurality of locations of the inspected object from the real time defect recorder 66 of FIG. 1, as well as the coordinates of each of the plurality of locations. The false alarm rate reducing unit 250 also receives reference information. The reference information may comprise binary database information pertaining to defect locations as identified by the defect coordinates and provided by database rasterizer 56 (FIG. 1), in the case of die to database comparisons. Alternatively, if a die to die comparison method is employed, the reference information may comprise gray reference information pertaining to the locations of the reference object corresponding to the locations identified by the defect coordinates.

False alarm rate reducing unit 250 reanalyzes each putative defect location, filters out false alarms and provides an output indication of the coordinates indicating the locations of true defects which is stored in a defect memory 252. False alarm reducing unit 250 also preferably categorizes the defects according to at least some of the following criteria: missing/extra chrome, edge/isolated/corner defect, size. The information regarding the location and categorization of the defects as identified by false alarm reducing unit 250 is stored in a defect memory 252. Preferably, the stored information is analyzed statistically by a statistical analysis unit 254 which may comprise any suitable statistical software package such as SAS.

Preferably, an operator display 256 such as a CRT provides an on-line display for the operator of the defect analysis process. The display preferably comprises a display of the defect images analyzed by the false alarm reducing unit 250.

The on-line display 256 enables the operator to review the defect images and, via a defect classification unit 258, to amend defect classifications. Preferably, the user may also indicate to the system that a particular putative defect designated by false alarm reducing unit 250 is a false alarm. Defect memory 252 may interface with a repair machine (not shown) such as a repair machine manufactured by Quantronix, Smithtown, N.Y., USA, to repair the reticle.

The defect post-processing unit 67 is preferably implemented in software as opposed to the defect processing units 32 and 64 of FIG. 1 which are implemented in hardware. A software embodiment of a preferred embodiment of post-processing unit 67 is provided in Appendix 5 (not printed).

A preferred method for reducing the false alarm rate and classifying defects is as follows:

The real time recorder 66 (FIG. 1) records the sampled gray image of the area around and including each putative defect pixel in the inspected object together with the relevant coordinates. The putative defect pixels are defined as those defects reported by defect detectors 32 and 64 of FIG. 1.

The first step in false alarm rate reduction is arrangement of the putative defect data and may comprise the following substeps:

clustering the data into groups of adjacently disposed or "connected" putative defect pixels;

for each cluster, constructing an "inspected putative defect image" which is a unified image of the inspected object in the vicinity of the current cluster of putative defect pixels; and extracting from the stored database a "corresponding reference image" which is that portion of the database corresponding to the inspected putative defect image.

A preferred false alarm rate reduction method may comprise the following steps:

1. Binarization of the inspected image and of the reference, if the reference is not represented in binary form, as explained above. This may be implemented using algorithms described in U.S. patent application Ser. No. 684,583 the disclosure of which is incorporated herein by reference. Preferably, the algorithms are software implemented.

2. Global matching of the binary representations of the inspected and reference images. The matching is global in the sense that the complete recorded area is taken into account. A preferred global matching technique is template matching in which the template is the inspected putative defect image, the search window is the reference image, and the match criteria is the minimum of the area of the XOR of the inspected putative defect image and the corresponding portion of the reference.

In order to decrease the computation load, the matching process is repeated more than once. The first repetition is performed on the two images at a relatively small resolution, such as a resolution reduced, relative to the original resolution, by a factor of between 2 to 8. In the first repetition, the search window is relatively large. Subsequent repetitions are performed on the two images at increasing resolutions until the original resolution is restored. In the subsequent repetitions, the size of the search window is gradually decreased. Matching techniques are described in Digital Picture Processing by A. Rosenfeld and A. Kak, Academic Press, 1982, Vol. 2, Sections 9.4 and 12.1.

3. Local matching of the binary representations of the inspected and reference putative images. This matching is local in the sense that only the subimage contained in the enclosing rectangle of the putative defect pixels is taken into account. This step may be implemented by the template matching step referred to hereinabove, however the template area is now the enclosing rectangle area and the resolution is the original binary resolution.

4. Computing a difference measure which may comprise one or both of:
   (a) the area of the XOR between the inspected and reference image portions after the local matching; and
   (b) the width of the XOR between the inspected and reference image portions after the local matching. The width measurement may be operationalized as an indication of whether the width does or does not exceed a certain threshold. This indication may be implemented by eroding a predetermined number of pixel layers. The predetermined number may be a function of the desired false alarm rate and of a predetermined threshold determining the minimum size of putative defect which is to be categorized as a genuine defect.

5. Classification of the matched images, thereby to provide an inventory of the area, size and type of defects.

Figure 14:
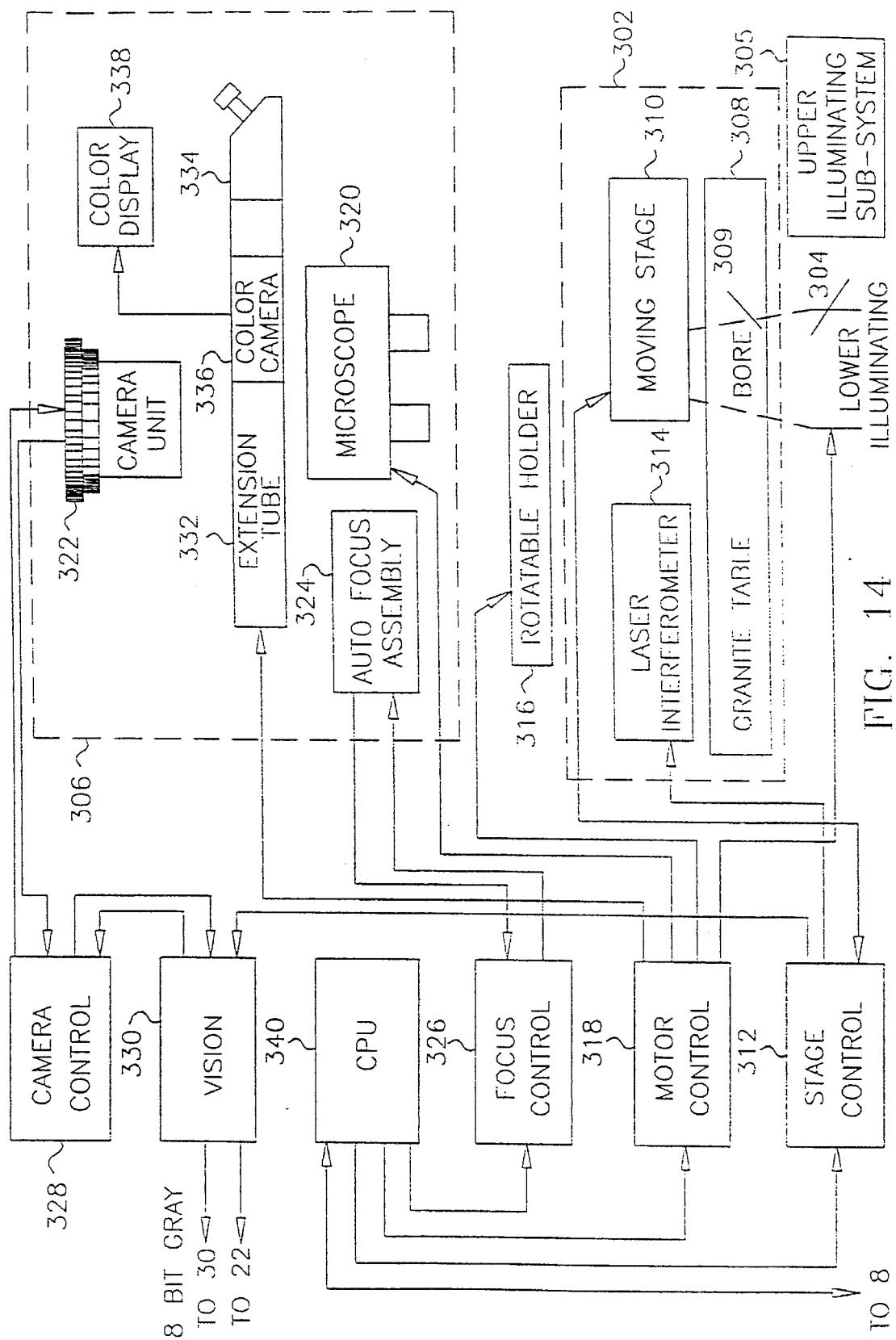
FIG. 14 is a combined block diagram and schematic front view of scanner 10 of FIG. 1.

Reference is now made to FIG. 14 which is a combined block diagram and schematic front view of a preferred embodiment of the scanner 10 of FIG. 1, constructed and operative according to a preferred embodiment of the present invention.

The scanner 10 comprises a bi-axis positioning subsystem denoted 302, lower and upper illuminating subsystems 304 and 305 respectively, and an image acquisitioning subsystem 306. The structure and the operation of each subsystem will now be described separately.

The bi-axis positioning subsystem 302 may be a Microglide L250 commercially available from Anorad Co., Haupauge, N.Y., USA and comprises a granite table 308 having a bore 309 and a moving stage 310 provided with linear motors (not shown), air bearings (not shown) and a laser interferometer 314. The position of the stage 310 as measured by the interferometer 314 is transmitted to a stage controller 312.

Supported above the stage 310 is a bi-axis positionable and rotatable holder 316 for holding the to-be-inspected reticle. The position and orientation of the holder 316 are controlled by a motor controller 318 via motors (not shown).

The reticle is illuminated by the lower illuminating subsystem 304 which is situated beneath the granite table 308 and which is described in detail with reference to FIG. 15. The apertures and filters of the subsystem 304 are motor driven under the control of motor controller 318.

The illuminated reticle is viewed by a microscope 320. The microscope 320 is preferably provided with a plurality of objective lenses with different magnifications, preferably standard magnifications. The magnified image of the reticle generated by the microscope 320 is acquisitioned by the CCD line array sensor of a camera unit 322. The reticle is maintained in focus by means of an autofocus assembly 324 which is controlled by a focus control unit 326. The selected objective is positioned with respect to the optical axis of microscope motor means (not shown) driven by the motor controller 318.

The timing and amplifying operations of the camera unit 322 are controlled by a camera controller 328. Trigger signals for camera controller 328 are generated by a vision unit 330 in response to signals received from a stage controller 312 which describe the coordinates of the stage 310.

The camera controller 328 transmits a digital video signal of raw 8 bit gray data to the vision unit 330. The vision unit 330 then processes this data to compensate for the non-uniformity of the response of the CCD sensor and provides an output of the processed final gray data to units 30 and 22 of FIG. 1.

Interposed between the microscope 320 and the camera 322 is an extension tube 332. The extension tube 332 relays the image generated by the microscope 320 to a trinocular 334 and to a color camera 336 for displaying the image on a color display 338.

The activities of the stage controller 312, the motor controller 318, the focus control 326 and the camera control 328 are controlled by a CPU 340 in accordance with control data sent to the scanner 10 by the main controller 8 of FIG. 1.

Figure 15A:
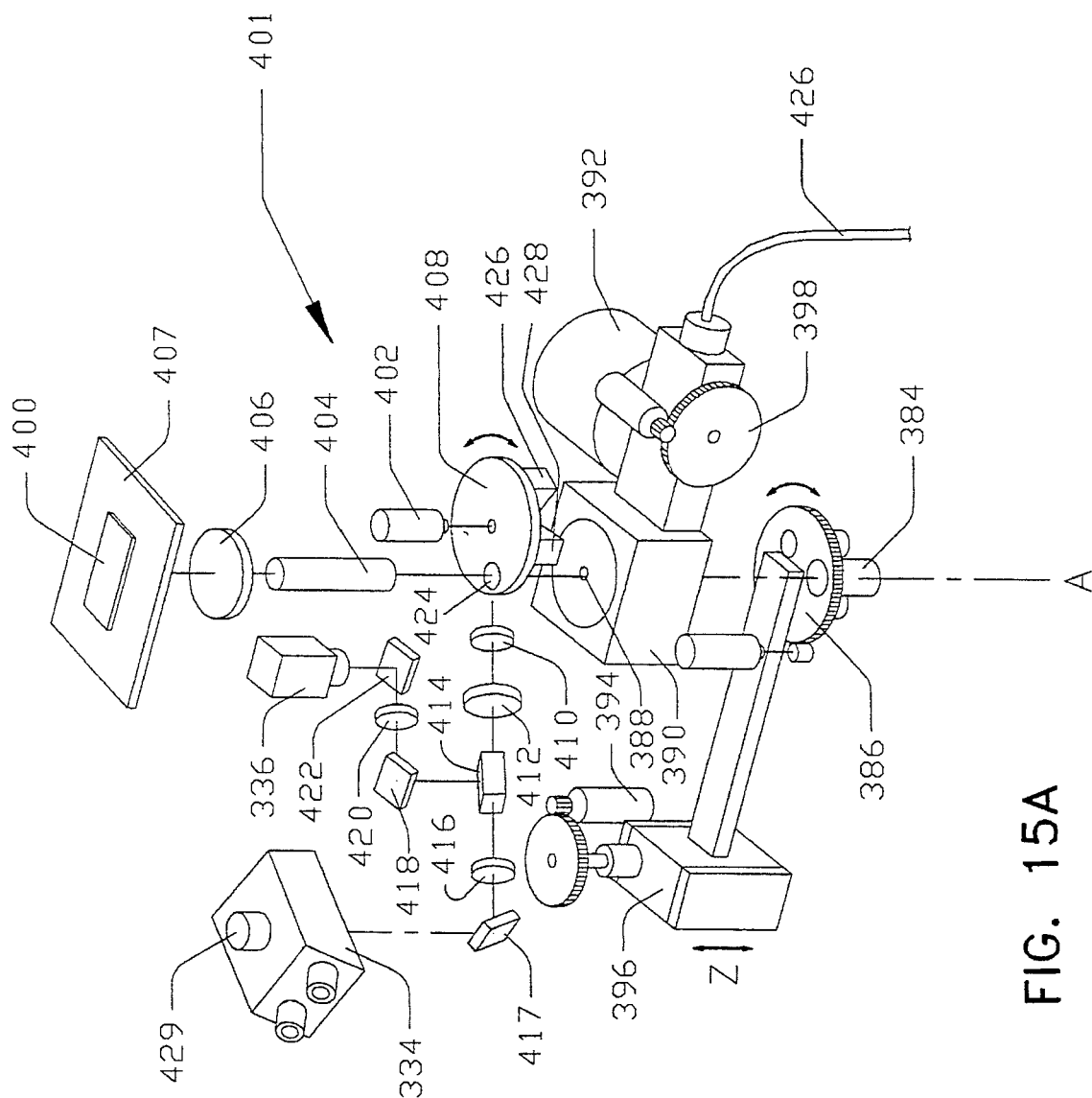
FIGS. 15/1 and 15/2 are, composed of FIGS. 15A and 15B, exploded views of the optical components of the scanner 10 of FIG. 1.
Figure 15B:
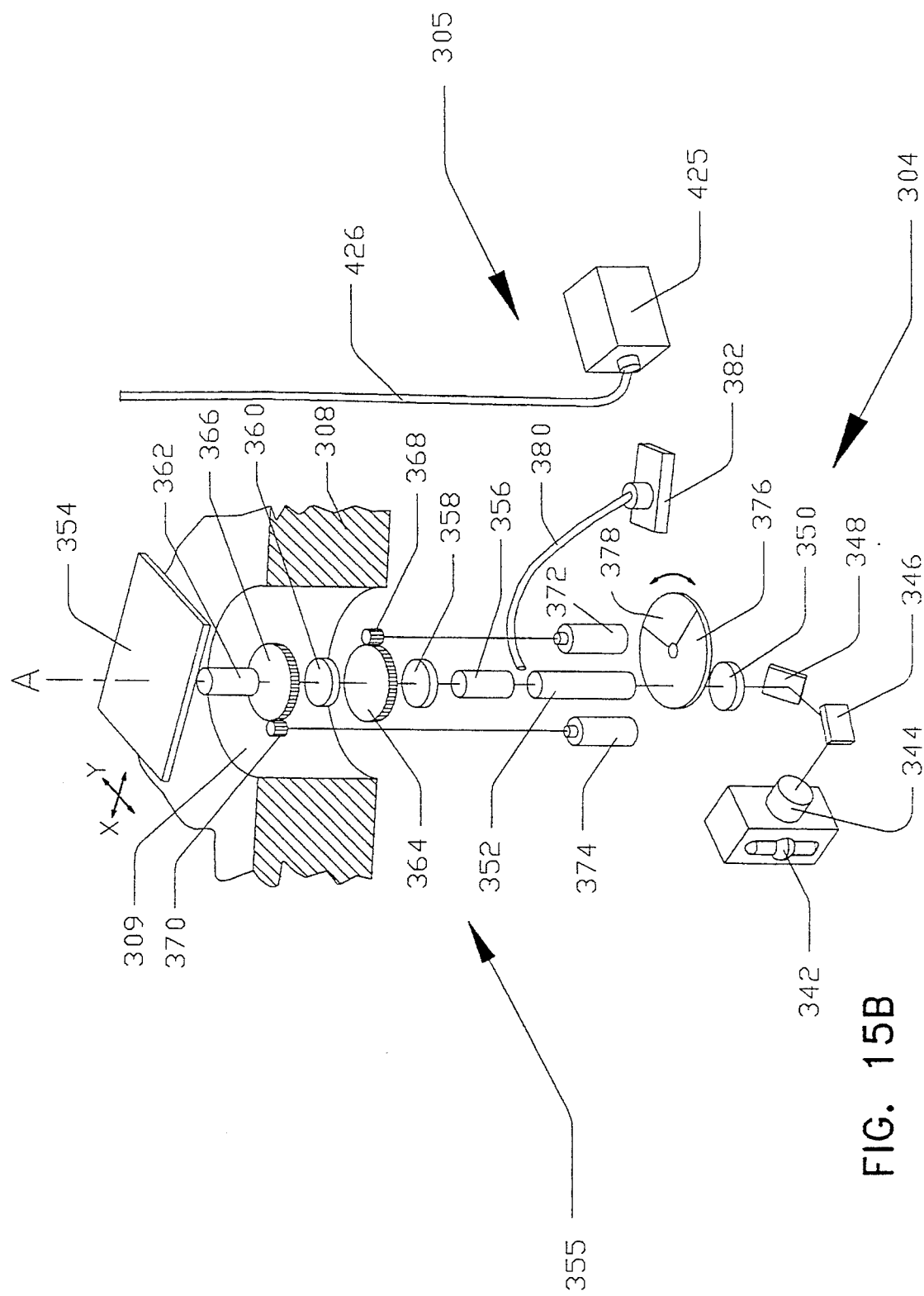

Reference is now made to FIG. 15, which is an exploded view of the optical components of the scanner 10 of FIG. 1.

The illuminating subsystem 304 preferably comprises a lamp housing 342 accommodating a lamp such as a high pressure mercury arc lamp and a collimating lens 344 having a high numerical aperture, preferably exceeding 0.5. The light beam emitted from the lamp is reflected by means of two "cold mirrors" 346 and 348 which filter out IR radiation and also provide the degree of freedom required to align the light beam along the optical axis of the optical system above the mirrors 346 and 348.

After the light beam deflects from mirror 348, focusing lens 350 generates a magnified image of the arc lamp on the lower surface of a cladrod 352, comprising a long, wide optical fiber. Cladrod 352 is configured and arranged such that the illumination on its upper surface remains uniform over the widest possible field of view required by the system, when the system requires the solidest possible angle for the highest numerical aperture, and for reticles of different thicknesses.

Preferred values for the diameter of the uniform illumination and for the numerical aperture are 2.8 mm and 0.55 respectively. These values allow reticles 354 of different thicknesses to be illuminated without employing compensating lenses and without moving any optical element.

The upper surface of the cladrod 352 is imaged by a lens assembly, generally denoted 355, comprising lenses 356, 358, 360 and 362. Lenses 356 and 358 control illuminated field width by generating an intermediate image of the upper surface of the cladrod 352 in the plane of the field aperture 364. Lens 356 collects the light from the cladrod 352. Lens 358 is a field lens which enables all the light to be collected from the upper surface of the cladrod 352 without "vignetting".

Lenses 360 and 362 image the intermediate image and the field aperture 364 on the upper surface of the reticle 354. Lens 360 operates as a field lens for lens 362 which is the condensing lens of the illuminating system 304. Condenser aperture 366 below the condenser lens 362 adjusts the numerical aperture of the condenser 360 to the particular requirements of the different system operating modes. Lenses 356 and 362 may be condenser lenses. Lenses 358 and 360 may be field lenses.

The lens assembly 355 preferably has no critical optical surfaces imaged on the reticle 354. The length of lens assembly 355 is sufficient to "transfer" the image of the cladrod upper surface through table 308 and moving stage 310 to the reticle.

The diameters of the field aperture 364 and the condenser aperture 366 are adjusted by gears 368 and 370, respectively, driven by motors 372 and 374, respectively. The motors 372 and 374 are controlled by the motor controlling unit 318 (FIG. 14) and are preferably situated below the granite table.

The illumination level for a particular operating mode of the inspection system 6 is achieved by use of a continuously varying ND filter wheel. As is well known in the art the transmission of such filters alters as a function of the rotational angle thereof. The actual illumination level present in the system is detected by the camera 322 which enables any deterioration in light generation by the arc light to be compensated for. By calibrating the light level detected by the camera 322 as a function of the angular position of ND filter 376 for each of the operating modes, CPU unit 340 can control the illumination level within the system via motor control unit 318. The ND filter 376 may be rotated by any suitable means such as motor and gear arrangement (not shown).

A metal plate 378 is provided above a portion of ND filter 376. Plate 378 is operative to block out the lower illuminating system when the scanner is in an "upper illuminating mode" or for the "dark level" calibration of the camera 322. The metal plate 378 and the ND filter wheel 376 are rotated by the same motor and controller.

A fiber optics light guide 380 is provided alongside lens 356 and aligned towards the upper surface of the cladrod 352 thereby enabling changes in the arc intensity to be detected and measured. The position of the light guide 380 minimizes changes as a result of arc movements.

The guide 380 samples the light emitted from the cladrod 352 and transmits the sample to a light detector 382. The electrical signals from the detector 382 are sent to the camera control unit 328 which measures and compensates for changes in arc intensity.

The microscope 320 is preferably of the "infinity corrected" type, and generates an enlarged image of the reticle 354 on a plane disposed approximately 103 mm thereabove. The microscope 320 primarily comprises three objectives 384 mounted on a rotatable objective wheel 386 and a telescope lens 388 such as that forming part of a "Leitz" Modulo-pack LAF unit 390.

The modulo-pack unit 390 further comprises an automatic focus sensor 392 for sensing the focussing error of the objective in the optical path of the microscope relative to the upper surface of the reticle 354. The error signal from the sensor 392 is sent to the focus controller 326 (FIG. 14) which, in turn, transmits a correcting signal to a focusing motor 394. The rotational movement of the motor 394 is converted to a vertical movement of the objective wheel 386 by means of a gear and slider arrangement 396 until a null signal is detected by the focus controller 326.

Different heights of various reticles 354 and of the objective lenses 384 can be accommodated for by altering the reference plane of the focus sensor 392. This is achieved by means of a focus off-set unit (not shown) incorporated within the Modulo-pack unit 390 which sets the height of the reference plane by a gear and motor 398 under the control of the motor controller 318 (FIG. 14). The image of the reticle that is generated by the microscope 320 may suffer from residual aberrations such as lateral color, astigmatism and curvature of the field. An optical subassembly 401 may be employed to obtain a diffraction limited image over a field as large as CCD sensor 400 which may comprise a 1024 element line array. The subassembly 401 typically comprises an eyepiece 404 and a doublet relay lens 406. The CCD sensor 400 is set on a fixture 407 having 3 translational and 2 rotational degrees of freedom for aligning the sensor 400 to the optical axis of the system.

For verification of the results of the reticle tests, an extension tube assembly 332 (see FIG. 14) is used to convey the image of the reticle to the trinocular unit 334 and the color TV camera 336. The extension tube 332 comprises a prism wheel 408, a cross reticle 410, a lens 312, and a beam splitter 414. Beam splitter 414 directs a portion of the beam to trinocular unit 334, via a lens 416 and a mirror 417. Beam splitter 414 directs another portion of the beam to the camera 336, via lens 420 and mirrors 418 and 422.

The prism wheel 408 is provided with an aperture 424 for straight line passage of the image to the CCD sensor 400 in a reticle scanning mode and carries two prisms 426 and 428 for reflecting the image to trinocular unit 334 and camera 336 for a reticle verification mode. The wheel 408 is rotated by motor 402.

A prism 426 is used when the reticle is illuminated by the lower (transmitted light) illuminating system 304. A prism 428 replaces prism 426 when the reticle is illuminated by a upper (incident light) illuminating subsystem 305. The difference between the prisms 426 and 428 is that the prism 426 is coated to block out UV radiation and to attenuate the visible light to a safe level.

The upper illuminating system 305 may employ a tungsten halogen lamp 425, preferably located under the granite table 308. The light is transmitted by a fiber optic light guide 426. When the reticle is illuminated by incident light, the scanner 10 is said to be in an "upper illumination mode" and all transmitted light from lamp 342 is blocked by rotating the filter wheel 376 and the blocking plate 378. To verify that the light from the lower illuminating system 304 is blocked, a pair of detectors 429 is provided in the camera opening of the trinocular 334. The output of detectors 429 is received by a control unit (not shown). If a signal above a safety threshold value is detected, the coated safety protecting prism is rotated into the optical path.

The terms "inspected object", "object to be inspected" and "patterned object" as employed in the present specification and claims are intended to include substantially any object such as but not limited to the following elements: flat panel displays, reticles, printed circuit boards, semiconductor wafers and photomasks.

The above terms are not intended to exclude objects whose surface has a continuous appearance such as blanks of any of the above elements.

It will be appreciated by persons skilled in the art that the present invention is not limited to what has been particularly shown and described hereinabove. Rather, the scope of the present invention is defined only by the claims that follow:

We claim:

1. An inspection method comprising: providing a patterned object to be inspected and compared with a reference;

inspecting the patterned object and providing an output of information relating to visually sensible characteristics of the patterned object, said output of information comprising gray level information regarding the patterned object;

converting said gray level information into binary level information regarding the patterned object, the gray level to binary level conversion being carried out at subpixel accuracy;

comparing binary level information relating to visually sensible characteristics of the patterned object to binary level information relating to corresponding visual sensible characteristics of the reference; and comparing gray level information relating to visually sensible characteristics of the patterned object to gray level information relating to corresponding visually sensible characteristics of the reference.

2. An inspection system comprising:

apparatus for comparing an inspected object to a reference and providing an output of information relating to visually sensible characteristics of the inspected object, said output of information comprising gray level information regarding the patterned object;

a binarizing unit operative to convert said gray level information into binary level information regarding the patterned object, the gray level to binary level conversion being carried out at subpixel accuracy;

binary level comparison apparatus for comparing binary level information relating to visually sensible characteristics of the inspected object to binary level information relating to visually sensible characteristics of the reference; and gray level comparison apparatus for comparing gray level information relating to visually sensible characteristics of the inspected object to gray level information relating to visually sensible characteristics of the reference.

3. An inspection system according to claim 2 and also comprising apparatus for providing information relating to visually sensible characteristics of the reference.

4. A system according to claim 15 and wherein said gray level comparison apparatus comprises apparatus for converting binary level information relating to visually sensible characteristics of said reference into gray level information.

5. A system according to claim 2 and wherein said binary level comparison apparatus is operative to sense differences between visually sensible characteristics of the inspected object and of the reference of at least a first minimum size and said gray level comparison apparatus is operative to sense differences between visually sensible characteristics of the inspected object and of the reference of at least a second minimum size smaller than said first minimum size.

6. An inspection system according to claim 2 and wherein said gray level comparison apparatus comprises:

first apparatus for sensing hill profiles and valley profiles in the information relating to visually sensible characteristics of the inspected object;

second apparatus for sensing hill profiles and valley profiles in the information relating to visually sensible characteristics of the reference; and apparatus for providing a defect indication when a hill profile or a valley profile of at least a sufficient level is sensed for a given location in the inspected object and not for a corresponding location in the reference.

7. An inspection system according to claim 6 and wherein said apparatus for providing a defect indication comprises:

apparatus responsive to selected information indicating the presence of selected visually sensible features at locations in the reference for preventing provision of an output indication of difference between the inspected object and the reference in respect of those locations.

8. An inspection system according to claim 6 and wherein said location in said reference is larger in area than said corresponding location in said inspected object.

9. An inspection system according to claim 2 and wherein said gray level comparison apparatus comprises apparatus responsive to selected information indicating the presence of selected visually sensible features at locations in the reference for preventing provision of an output indication of difference between the inspected object and the reference in respect of those locations.

10. An inspection system according to claim 2 wherein said binary level comparison apparatus comprises difference indicating apparatus for providing an indication of differences between visually sensible characteristics of the inspected object and the reference and wherein said difference indicating apparatus comprises apparatus for filtering out differences within a selected magnitude range.

11. An inspection system according to claim 10 and wherein said binary level comparison apparatus comprises at least one of the following:

at least one SUBTRACTION logic operator; and at least one XOR logic operator.

12. An inspection system according to claim 10 and wherein said apparatus for filtering comprises an EROSION operator.

13. An inspection system according to claim 10 and wherein said means for filtering comprises an ACCEPTANCE operator.

14. An inspection system according to claim 2 wherein said means for comparing comprises means for receiving information relating to the visually sensible characteristics of the reference from a database precursor of said reference.

15. A system according to claim 2 and wherein said apparatus for comparing comprises apparatus for inspecting said reference and for providing information relating to visually sensible characteristics of the reference.

16. An inspection system according to claim 2 wherein said apparatus for comparing comprises:

apparatus for receiving information relating to the visually sensible characteristics of the reference from a database precursor of said reference;

apparatus for inspecting said reference and providing information relating to the visually sensible characteristics of the reference; and apparatus for selectably activating the apparatus for receiving or the apparatus for inspecting.

17. An inspection system according to claim 2 and wherein said apparatus for comparing comprises apparatus for varying the magnification at which at least the inspected object is inspected.

18. An inspection system according to claim 17 wherein said apparatus for comparing also comprises apparatus for automatically controlling, as a function of said magnification, at least one parameter relating to the inspection of at least the inspected object.

19. An inspection system comprising:

apparatus for providing at least one representation of visually sensible characteristics of an inspected object;

first apparatus for comparing an individual one of said at least one representation of said inspected object to a reference and providing an output indication of differences; and second apparatus for comparing an individual one of said at least one representation to a reference, thereby to complement said first apparatus by enhancing said indication of differences provided by said first apparatus, wherein at least one of said first and second apparatus employ subpixel binarization to align the inspected object to the reference.

20. An inspection system comprising:

apparatus for comparing an inspected object to a reference and providing an output of information relating to visually sensible characteristics of the inspected object;

first apparatus for providing an indication of differences between the inspected object and the reference; and second apparatus for automatically carrying out a second inspection of visually sensible characteristics of at least some areas of the inspected object and for complementing said first apparatus and comprising apparatus for enhancing said indication of differences provided by said first apparatus, wherein at least one of said first apparatus and second apparatus performs alignment based on subpixel binarization.

21. An inspection system according to claim 20 and wherein said apparatus for enhancing comprises apparatus for preventing provision of said output indication of difference in at least some areas of said inspected object, thereby to reduce the false alarm rate of said first apparatus.

22. An inspection system according to claim 20 and wherein said second apparatus comprises apparatus for providing an output indication of differences between the inspected object and the reference not detected by said first apparatus.

23. An inspection method comprising:

providing a patterned object to be inspected and compared with a reference;

carrying out a first inspection of the patterned object and providing an output of information relating to visually sensible characteristics of the patterned object;

comparing the information relating to the visually sensible characteristics of the patterned object to the reference, thereby to provide an indication of differences between the patterned object and the reference; and automatically carrying out a second inspection of the visually sensible characteristics of at least some areas of the patterned object thereby to enhance said indication of differences, wherein at least one of said first and second inspections include alignment based on subpixel binarization.

24. An inspection method comprising:

providing a patterned object to be inspected and compared with a reference;

carrying out a first inspection of the patterned object and providing an output of information relating to visually sensible characteristics of the patterned object;

comparing the information relating to the visually sensible characteristics of the patterned object to the reference, thereby to provide an indication of differences between the patterned object and the reference; and automatically carrying out a second inspection of the visually sensible characteristics of at least some areas of the patterned object thereby to enhance said indication of differences, wherein the second inspection of characteristics of each reinspected area of the patterned object is off-line relative to the first inspection of the patterned object.

25. An inspection method comprising:

providing at least one representation of visually sensible characteristics of an inspected object;

comparing an individual one of said at least one representations of said inspected object to a reference and providing an output indication of differences; and comparing an individual one of said at least one representations to a reference, thereby to complement said first comparing operation by enhancing said output indication of differences, wherein at least one of said first comparing operation and said second comparing operation employ subpixel binarization to align the inspected object to the reference.

26. A method according to claim 1 and wherein said comparing comprises varying the magnification at which at least the inspected object is inspected.

27. An inspection method according to claim 26 wherein said comparing also comprises automatically controlling, as a function of said magnification, at least one parameter relating to the inspection of at least the inspected object.

* * * * *